United States Patent
Yoneda et al.

(10) Patent No.: US 11,847,195 B2
(45) Date of Patent: Dec. 19, 2023

(54) AUTHENTICATION SYSTEM AND METHOD FOR RECORDING UNLOCKING HISTORY USING AUTHENTICATION SYSTEM

(71) Applicant: SEMICONDUCTOR ENERGY LABORATORY CO., LTD., Atsugi (JP)

(72) Inventors: Seiichi Yoneda, Kanagawa (JP); Yusuke Negoro, Osaka (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 204 days.

(21) Appl. No.: 17/279,637

(22) PCT Filed: Sep. 26, 2019

(86) PCT No.: PCT/IB2019/058152
§ 371 (c)(1),
(2) Date: Mar. 25, 2021

(87) PCT Pub. No.: WO2020/070590
PCT Pub. Date: Apr. 9, 2020

(65) Prior Publication Data
US 2021/0342423 A1    Nov. 4, 2021

(30) Foreign Application Priority Data

Oct. 5, 2018 (JP) .................. 2018-189681

(51) Int. Cl.
*G06F 21/31* (2013.01)
*G06F 16/22* (2019.01)
(Continued)

(52) U.S. Cl.
CPC .............. *G06F 21/31* (2013.01); *G06F 16/22* (2019.01); *G06V 10/143* (2022.01);
(Continued)

(58) Field of Classification Search
None
See application file for complete search history.

(56) References Cited

U.S. PATENT DOCUMENTS 8,660,318 B2 * 2/2014 Komura ................. G06V 40/12
382/115
8,736,587 B2   5/2014 Yamazaki
(Continued)

FOREIGN PATENT DOCUMENTS

CN    104751155 A    7/2015
EP      2495699 A    9/2012
(Continued)

OTHER PUBLICATIONS

Bak JY, Yang S, Yoon SM. Transparent Al—In—Zn—O Oxide semiconducting films with various in composition for thin-film transistor applications. Ceramics International. Apr. 1, 2013;39(3):2561-6. (Year: 2013).*

(Continued)

*Primary Examiner* — James R Turchen
(74) *Attorney, Agent, or Firm* — Fish & Richardson P.C.

(57) ABSTRACT

A novel authentication system is provided. In addition, a method for recording an unlocking history is provided. The authentication system includes an arithmetic device and an input/output device. The arithmetic device supplies first control data and second control data, and is supplied with a sensor signal. The input/output device includes an electric lock and a reading portion, and the electric lock is unlocked on the basis of the second control data. The reading portion is supplied with the first control data, supplies the sensor signal, and includes a light-emitting element and a pixel array. The light-emitting element emits light including infrared rays, the pixel array includes pixels, the pixels each include an imaging circuit and a photoelectric conversion element, the imaging circuit is electrically connected to the (Continued)

photoelectric conversion element, the imaging circuit includes a transistor, and the transistor includes an oxide semiconductor film.

7 Claims, 20 Drawing Sheets

(51) Int. Cl.

| | | |
|---|---|---|
| *H01L 25/16* | (2023.01) | |
| *G06V 10/143* | (2022.01) | |
| *G06V 40/13* | (2022.01) | |
| *G06V 40/14* | (2022.01) | |
| *H01L 27/146* | (2006.01) | |
| *H01L 27/15* | (2006.01) | |
| *H01L 29/786* | (2006.01) | |
| *H01L 31/12* | (2006.01) | |
| *G06V 40/12* | (2022.01) | |

(52) U.S. Cl.
CPC .......... *G06V 40/1318* (2022.01); *G06V 40/14* (2022.01); *H01L 25/167* (2013.01); *G06V 40/1347* (2022.01); *G06V 40/1365* (2022.01); *H01L 27/14616* (2013.01); *H01L 27/15* (2013.01); *H01L 29/7869* (2013.01); *H01L 31/12* (2013.01)

(56) References Cited

U.S. PATENT DOCUMENTS

| | | | |
|---|---|---|---|
| 9,559,239 | B2 | 1/2017 | Yamamoto |
| 9,965,669 | B2 | 5/2018 | Yamamoto |
| 2010/0007632 | A1* | 1/2010 | Yamazaki ............. G06F 3/0421 345/175 |
| 2012/0201431 | A1 | 8/2012 | Komura et al. |
| 2014/0016833 | A1* | 1/2014 | Ide .......................... G06V 40/10 382/115 |
| 2014/0299879 | A1 | 10/2014 | Yamazaki |
| 2015/0180866 | A1* | 6/2015 | Hama ..................... G06F 21/32 726/6 |
| 2015/0187980 | A1 | 7/2015 | Yamamoto |
| 2015/0279884 | A1* | 10/2015 | Kusumoto ........ H01L 27/14643 257/43 |
| 2017/0043160 | A1* | 2/2017 | Goodall ................. A61B 5/318 |
| 2017/0154202 | A1* | 6/2017 | Gottemukkula ........ G06F 18/22 |
| 2017/0325721 | A1* | 11/2017 | Matsuda .............. A61B 5/0059 |
| 2017/0337412 | A1* | 11/2017 | Bhat .................. G06V 40/1318 |
| 2017/0344839 | A1* | 11/2017 | Abe .................... G06V 40/1347 |
| 2018/0089527 | A1* | 3/2018 | Aoki .................. G06V 10/7715 |
| 2018/0336428 | A1* | 11/2018 | Ichige ..................... G01N 21/01 |
| 2019/0035842 | A1* | 1/2019 | Hirase ............... H01L 27/14609 |
| 2019/0080153 | A1* | 3/2019 | Kalscheur ............ G06V 40/166 |
| 2019/0125221 | A1* | 5/2019 | Kobayashi ............ G06T 1/0007 |
| 2019/0318361 | A1* | 10/2019 | Hurst ................... G06Q 20/383 |
| 2020/0356751 | A1* | 11/2020 | Matsuda ................. G06T 1/00 |

FOREIGN PATENT DOCUMENTS

| | | |
|---|---|---|
| EP | 3401470 A | 11/2018 |
| JP | 2006-149634 A | 6/2006 |
| JP | 2010-040042 A | 2/2010 |
| JP | 2011-101095 A | 5/2011 |
| JP | 2011-236730 A | 11/2011 |
| JP | 2015-125663 A | 7/2015 |
| TW | 201732682 | 9/2017 |
| TW | 201814573 | 4/2018 |
| WO | WO-2011/052085 | 5/2011 |
| WO | WO-2017/119295 | 7/2017 |
| WO | WO-2018/052003 | 3/2018 |

OTHER PUBLICATIONS

Matt Golowczynski; Digital camera sensors explained; https://www.whatdigitalcamera.com/author/mattgolowczynski; Jun. 23, 2016 (Year: 2016).*

What is the difference between CCD and CMOS image sensors in a digital camera?; https://electronics.howstuffworks.com/cameras-photography/digital/digital-camera.htm; Nov. 29, 2016 (Year: 2016).*

Mehta S, Patel A, Mehta J. CCD or CMOS Image sensor for photography. In2015 international conference on communications and signal processing (ICCSP) Apr. 2, 2015 (pp. 0291-0294). IEEE. (Year: 2015).*

International Search Report (Application No. PCT/IB2019/058152) dated Nov. 19, 2019.

Written Opinion (Application No. PCT/IB2019/058152) dated Nov. 19, 2019.

* cited by examiner

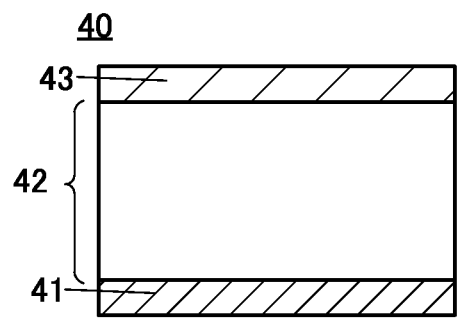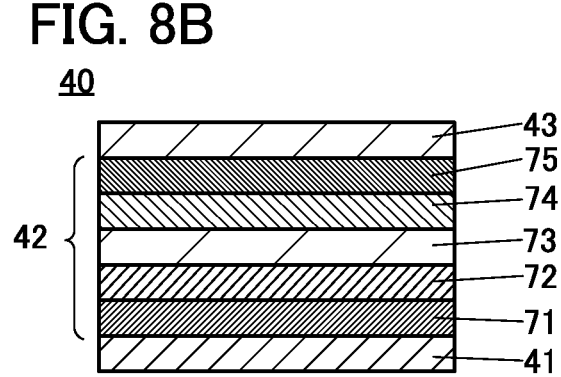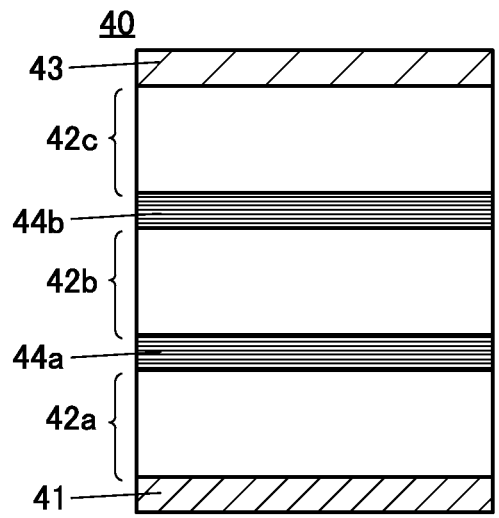

FIG. 14A

| | | | | | | | | |
|---|---|---|---|---|---|---|---|---|
| Line[1] | Rn−1 | En | | Rn | En+1 | | | |
| Line[2] | En−1 | Rn−1 | En | | Rn | En+1 | | |
| Line[3] | En−1 | | Rn−1 | En | | Rn | | En+1 |
| ⋮ | | | | | | | | |
| Line[M] | En−1 | | Rn−1 | En | | | Rn | |

FIG. 14B

| | | | | | |
|---|---|---|---|---|---|
| Line[1] | En | Rn | | | En+1 |
| Line[2] | En | | Rn | | En+1 |
| Line[3] | En | | | Rn | En+1 |
| ⋮ | | | | | |
| Line[M] | En | | | Rn | En+1 |

AUTHENTICATION SYSTEM AND METHOD FOR RECORDING UNLOCKING HISTORY USING AUTHENTICATION SYSTEM

CROSS REFERENCE TO RELATED APPLICATIONS

This application is a U.S. National Phase Application under 35 U.S.C. § 371 of International Application PCT/IB2019/058152, filed on Sep. 26, 2019, which is incorporated by reference and claims the benefit of a foreign priority application filed in Japan on Oct. 5, 2018, as Application No. 2018-189681.

TECHNICAL FIELD

One embodiment of the present invention relates to an authentication system or a method for recording an unlocking history using the authentication system.

Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Thus, more specifically, examples of the technical field of one embodiment of the present invention disclosed in this specification include a semiconductor device, a display device, a light-emitting device, a power storage device, a memory device, a driving method thereof, and a manufacturing method thereof.

BACKGROUND ART

An authentication device for living body communication that performs authentication by communication via a living body with a terminal device for living body communication worn on a living body is known (Patent Document 1).

The authentication device for living body communication includes an electric lock for communication provided to be proximate to a living body; a transmitting circuit that transmits a startup signal through a communication electrode; a receiving circuit that receives a reception signal including an individual identification ID through the communication electrode; a proximity determining portion that determines whether a living body is proximate to the communication electrode on the basis of the reception signal level at a timing when the startup signal is intermittently transmitted through the receiving circuit portion; and a comparing portion that compares on the basis of the individual identification ID, and is provided with an authentication control portion that allows authentication when a living body is determined to be proximate and the comparison result is verified.

REFERENCE

Patent Document

[Patent Document 1] Japanese Published Patent Application No. 2011-101095

SUMMARY OF THE INVENTION

Problems to be Solved by the Invention

An object of one embodiment of the present invention is to provide an authentication system that is highly convenient or reliable. Another object is to provide a method for recording an unlocking history, which is highly convenient or reliable. Another object is to provide a novel authentication system, a novel method for recording an unlocking history, or a novel semiconductor device.

Note that the descriptions of these objects do not preclude the existence of other objects. One embodiment of the present invention does not have to achieve all these objects. Objects other than these are apparent from the descriptions of the specification, the drawings, the claims, and the like, and objects other than these can be derived from the descriptions of the specification, the drawings, the claims, and the like.

Means for Solving the Problems

One embodiment of the present invention is an authentication system including an arithmetic device and an input/output device.

The arithmetic device supplies a first control data and a second control data, and the arithmetic device is supplied with a sensor signal.

The input/output device includes an electric lock and a reading portion.

The electric lock is unlocked on the basis of the second control data. The reading portion is supplied with the first control data and supplies the sensor signal, and the reading portion includes a light-emitting element and a pixel array.

The light-emitting element emits light including infrared rays, the pixel array includes pixels, and the pixels each include an imaging circuit and a photoelectric conversion element.

The imaging circuit is electrically connected to the photoelectric conversion element, and the imaging circuit includes a transistor. The transistor includes an oxide semiconductor film, and the photoelectric conversion element includes an organic semiconductor film.

Thus, an image of a physical feature can be taken, for example. Alternatively, an image of a vein spread or a vein arrangement pattern can be taken, for example. Alternatively, data included in a physical feature can be extracted. Alternatively, a security level can be increased. As a result, a novel authentication system that is highly convenient or reliable can be provided.

Another embodiment of the present invention is the authentication system in which the above arithmetic device includes an arithmetic portion and a memory portion.

The memory portion stores a program and a first database.

The arithmetic portion extracts a feature value from the sensor signal on the basis of the program, and the arithmetic portion examines the feature value using the first database.

The arithmetic portion supplies the second control data on the basis of the examination result.

In this manner, an individual having a predetermined physical feature can be authenticated. Alternatively, the security level can be increased. As a result, a novel authentication system that is highly convenient or reliable can be provided.

Another embodiment of the present invention is the authentication system in which the above memory portion stores a second database.

The arithmetic portion records an unlocking history in the second database on the basis of the examination result.

Accordingly, the unlocking history can be recorded. Alternatively, the unlocking history can be recorded in association with an individual having a predetermined physical feature. Alternatively, the security level can be increased. As a result, a novel authentication system that is highly convenient or reliable can be provided.

Another embodiment of the present invention is the authentication system in which the above pixel includes a first layer and a second layer.

The first layer includes a first transistor and a second transistor, and the second layer includes a light-emitting element and a photoelectric conversion element.

One of a source and a drain of the first transistor is electrically connected to one electrode of the light-emitting element, and one of a source and a drain of the second transistor is electrically connected to one electrode of the photoelectric conversion element.

Another embodiment of the present invention is the authentication system in which the above oxide semiconductor film contains In, Zn, and M (M is Al, Ti, Ga, Sn, Y, Zr, La, Ce, Nd, or Hf).

Thus, the number of optical components such as a lens can be reduced. Alternatively, the thickness can be made small. Alternatively, wide-range imaging can be performed. Furthermore, the area can be easily increased. Alternatively, an image of a proximate subject can be captured. Alternatively, high-resolution imaging can be performed. As a result, a novel authentication system that is highly convenient or reliable can be provided.

Another embodiment of the present invention is a method for recording an unlocking history including a first step to a seventh step.

In the first step, imaging is performed to obtain a sensor signal.

In the second step, a program proceeds to the third step in the case where a change exceeding a predetermine level is observed in the sensor signal, and the program proceeds to the first step in the case where only a change less than or equal to the predetermined level is observed.

In the third step, imaging is performed to obtain a sensor signal.

In the fourth step, a feature value is extracted from the sensor signal.

In the fifth step, the feature value is examined using a first database. The program proceeds to the sixth step in the case where the first database includes data matching the feature value, and the program proceeds to the first step in the case where the first database includes no data matching the feature value.

In the sixth step, second control data is supplied to unlock an electric lock.

In the seventh step, the unlocking history is recorded in a second database.

In this manner, the unlocking history can be recorded in the second database. Alternatively, the unlocking history can be recorded in association with an individual having a predetermined physical feature. Alternatively, the security level can be increased. As a result, a novel method for recording an unlocking history, which is highly convenient or reliable, can be provided.

Although the block diagram in which components are classified by their functions and shown as independent blocks is shown in the drawings attached to this specification, it is difficult to completely divide actual components according to their functions and one component can relate to a plurality of functions.

In this specification, the names of a source and a drain of a transistor interchange with each other depending on the polarity of the transistor and the levels of potentials applied to the terminals. In general, in an n-channel transistor, a terminal to which a lower potential is applied is called a source, and a terminal to which a higher potential is applied is called a drain. In a p-channel transistor, a terminal to which a lower potential is applied is called a drain, and a terminal to which a higher potential is applied is called a source. In this specification, for the sake of convenience, the connection relation of a transistor is sometimes described assuming that the source and the drain are fixed; in reality, the names of the source and the drain interchange with each other according to the above relation of the potentials.

In this specification, a source of a transistor means a source region that is part of a semiconductor film functioning as an active layer or a source electrode connected to the above semiconductor film. Similarly, a drain of a transistor means a drain region that is part of the above semiconductor film or a drain electrode connected to the semiconductor film. Moreover, a gate means a gate electrode.

In this specification, a state in which transistors are connected in series means, for example, a state in which only one of a source and a drain of a first transistor is connected to only one of a source and a drain of a second transistor. In addition, a state in which transistors are connected in parallel means a state in which one of a source and a drain of a first transistor is connected to one of a source and a drain of a second transistor and the other of the source and the drain of the first transistor is connected to the other of the source and the drain of the second transistor.

In this specification, connection means electrical connection and corresponds to a state in which a current, a voltage, or a potential can be supplied or transmitted. Accordingly, a state of being connected does not necessarily mean a state of being directly connected and also includes, in its category, a state of being indirectly connected through a circuit element such as a wiring, a resistor, a diode, or a transistor that allows a current, a voltage, or a potential to be supplied or transmitted.

In this specification, even when independent components are connected to each other in a circuit diagram, there is actually a case where one conductive film has functions of a plurality of components such as a case where part of a wiring functions as an electrode, for example. Connection in this specification also includes such a case where one conductive film has functions of a plurality of components, in its category.

Furthermore, in this specification, one of a first electrode and a second electrode of a transistor refers to a source electrode and the other refers to a drain electrode.

Effect of the Invention

According to one embodiment of the present invention, a novel authentication system that is highly convenient or reliable can be provided. Alternatively, a novel method for recording unlocking history, which is highly convenient or reliable, can be provided. Alternatively, a novel authentication system, a novel method for recording unlocking history, or a novel semiconductor device can be provided.

Note that the descriptions of the effects do not preclude the existence of other effects. Note that one embodiment of the present invention does not have to have all these effects. Effects other than these will be apparent from the descriptions of the specification, the drawings, the claims, and the like and effects other than these can be derived from the descriptions of the specification, the drawings, the claims, and the like.

BRIEF DESCRIPTION OF THE DRAWINGS

FIG. 8A to FIG. 8C are diagrams illustrating structure examples of a light-emitting element.

FIG. 14A is a diagram illustrating a rolling shutter system and FIG. 14B is a diagram illustrating a global shutter system.

MODE FOR CARRYING OUT THE INVENTION

Figure 1A:
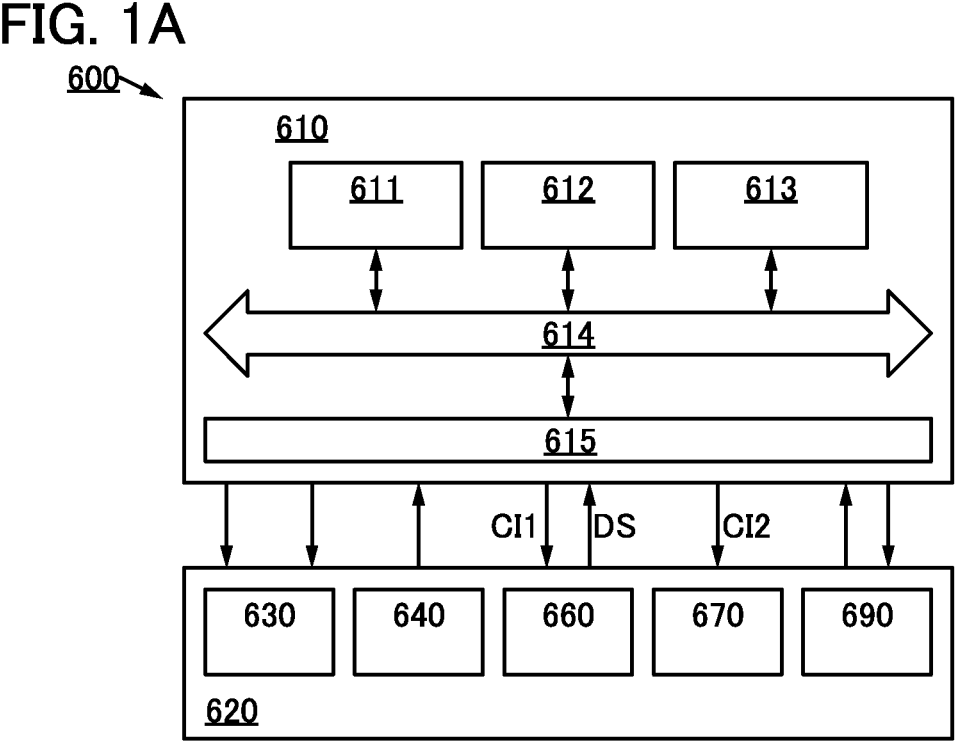
FIG. 1A to FIG. 1E are diagrams illustrating a structure of an authentication system of one embodiment.
Figure 1B:
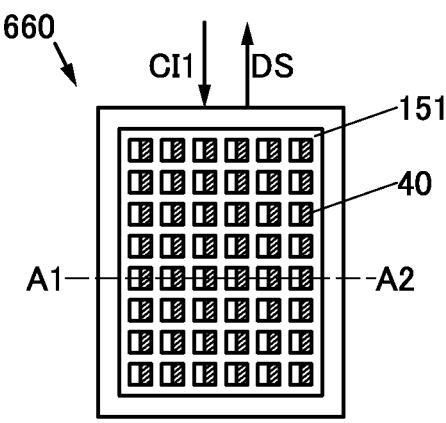

An authentication system of one embodiment of the present invention includes an arithmetic device and an input/output device. The arithmetic device supplies a first control data and second control data, and is supplied with a sensor signal. The input/output device includes an electric lock and a reading portion, and the electric lock is unlocked on the basis of the second control data. The reading portion is supplied with the first control data, supplies the sensor signal, and includes a light-emitting element and a pixel array. The light-emitting element emits light including infrared rays, the pixel array includes pixels, the pixels each include an imaging circuit and a photoelectric conversion element, the imaging circuit is electrically connected to the photoelectric conversion element, the imaging circuit includes a transistor, and the transistor includes an oxide semiconductor film. The photoelectric conversion element includes an organic semiconductor film.

Thus, an image of a physical feature can be taken, for example. Alternatively, an image of a vein spread or a vein arrangement pattern can be taken, for example. Alternatively, data included in a physical feature can be extracted. Alternatively, a security level can be increased. As a result, a novel authentication system that is highly convenient or reliable can be provided.

Embodiments will be described in detail with reference to the drawings. Note that the present invention is not limited to the following descriptions, and it will be readily appreciated by those skilled in the art that modes and details of the present invention can be modified in various ways without departing from the spirit and scope of the present invention. Thus, the present invention should not be construed as being limited to the descriptions in the following embodiments.

Note that in structures of the present invention described below, the same portions or portions having similar functions are denoted by the same reference numerals in different drawings, and a description thereof is not repeated. Furthermore, the same hatch pattern is used for the portions having similar functions, and the portions are not especially denoted by reference numerals in some cases.

The position, size, range, or the like of each component illustrated in drawings does not represent the actual position, size, range, or the like in some cases for easy understanding. Therefore, the disclosed invention is not necessarily limited to the position, size, range, or the like disclosed in the drawings.

Note that the term "film" and the term "layer" can be interchanged with each other depending on the case or circumstances. For example, the term "conductive layer" can be changed into the term "conductive film". As another example, the term "insulating film" can be changed into the term "insulating layer".

In this specification and the like, a metal oxide is an oxide of metal in a broad sense. Metal oxides are classified into an oxide insulator, an oxide conductor (including a transparent oxide conductor), an oxide semiconductor (also simply referred to as an OS), and the like. For example, in the case where a metal oxide is used in a semiconductor layer of a transistor, the metal oxide is referred to as an oxide semiconductor in some cases. That is, an OS FET can also be called a transistor including a metal oxide or an oxide semiconductor.

Furthermore, in this specification and the like, a metal oxide containing nitrogen is also collectively referred to as a metal oxide in some cases. A metal oxide containing nitrogen may be referred to as a metal oxynitride.

Embodiment 1

In this embodiment, structures of an authentication system of one embodiment of the present invention will be described with reference to FIG. 1, FIG. 2, and FIG. 11 to FIG. 13.

FIG. 1 shows diagrams illustrating a structure of the authentication system of one embodiment of the present invention. FIG. 1A is a block diagram of the authentication system of one embodiment of the present invention. FIG. 1B is a top view of a reading portion used in the authentication system of one embodiment of the present invention, and FIG. 1C is a cross-sectional view taken along a cutting line A1-A2 in FIG. 1B. FIG. 1D and FIG. 1E are schematic views each illustrating a situation where a palm image is captured using the reading portion of the authentication system of one embodiment of the present invention.

Figure 2:
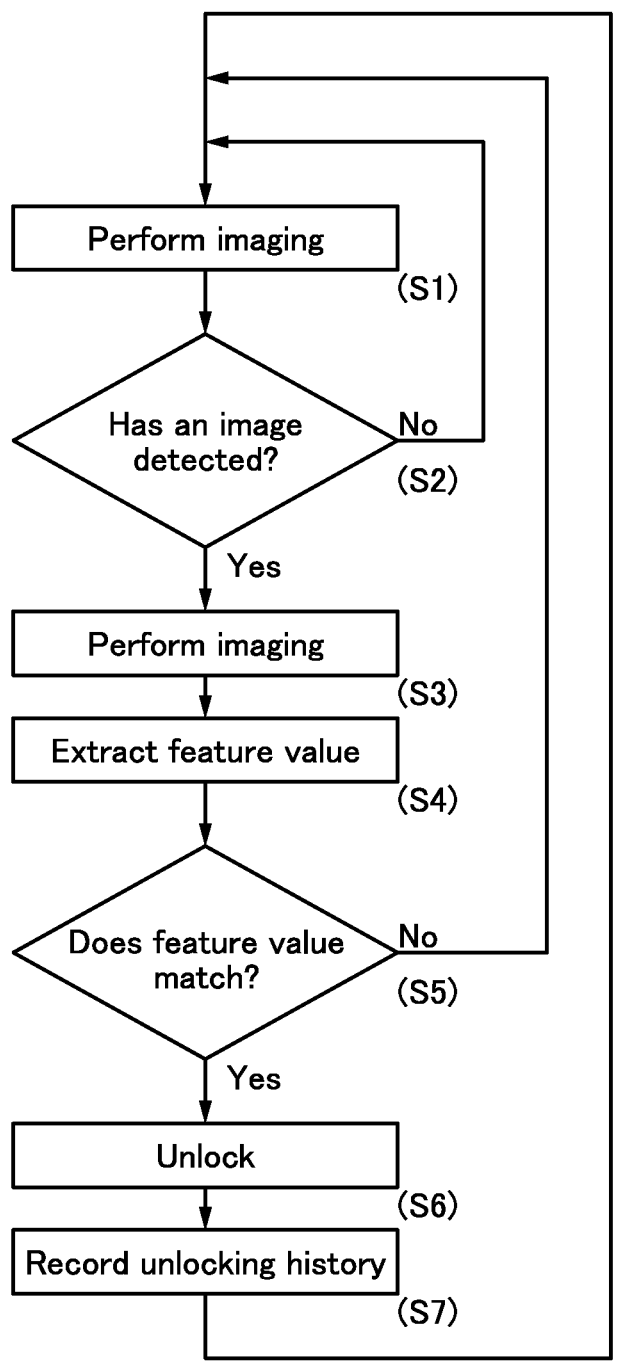
FIG. 2 is a diagram showing a method for recording an unlocking history using an authentication system of one embodiment.

FIG. 2 is a flow chart showing a method for recording an unlocking history using the authentication system of one embodiment of the present invention.

Figure 11:
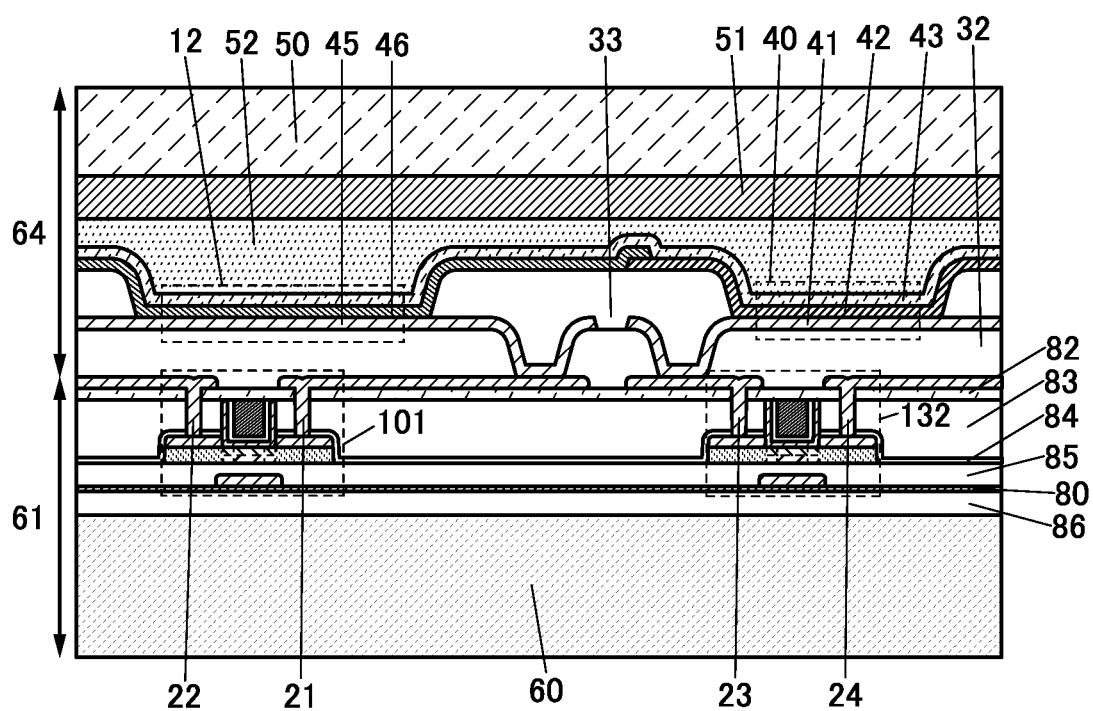
FIG. 11 is a diagram illustrating a structure example of a semiconductor device.

FIG. 11 is a cross-sectional view illustrating a structure of a pixel of a semiconductor device that can be used for the authentication system of one embodiment of the present invention.

Figure 12:
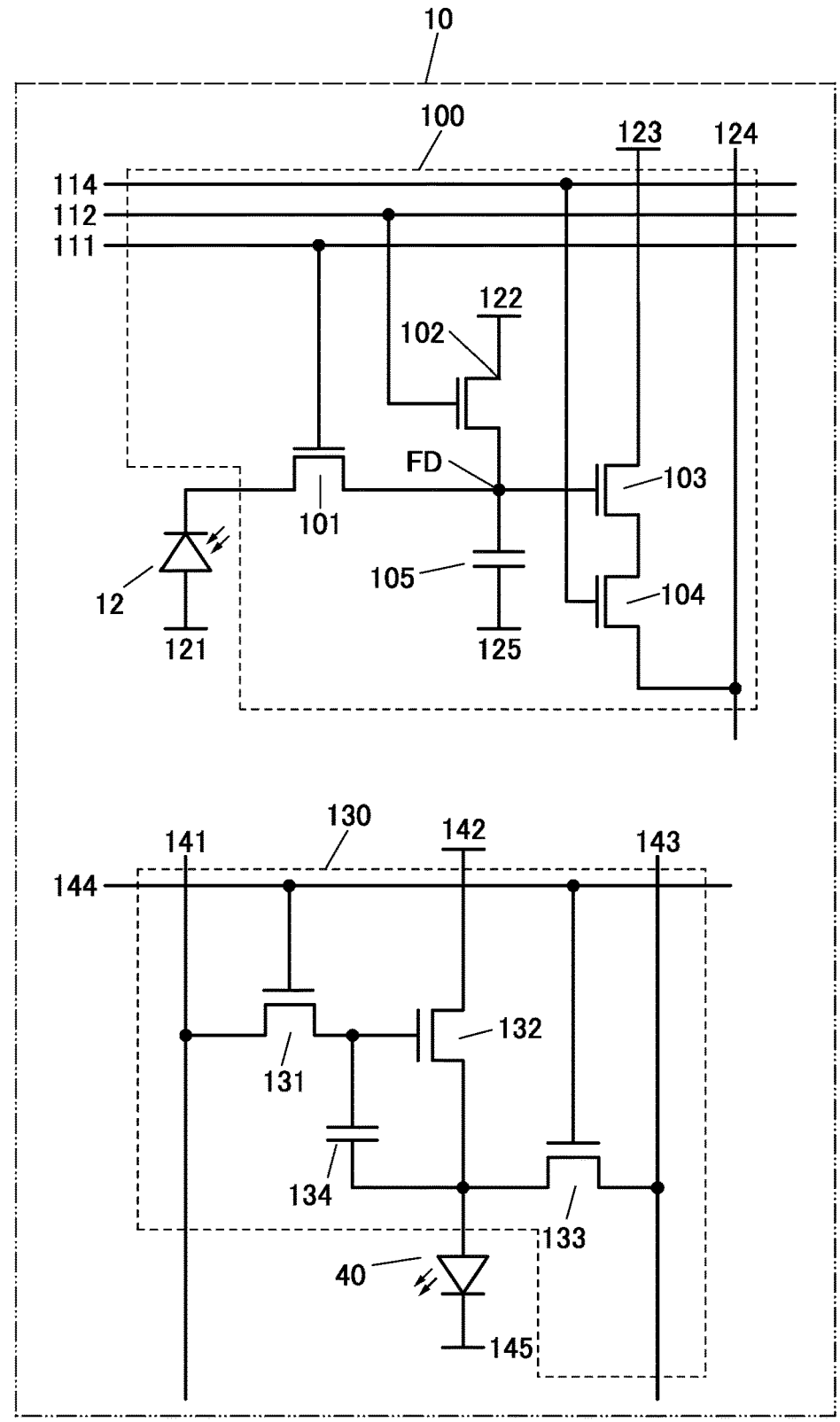
FIG. 12 is a diagram illustrating a configuration example of a pixel.

FIG. 12 is a circuit diagram illustrating a configuration of the pixel of the semiconductor device that can be used for the authentication system of one embodiment of the present invention.

FIG. 13 shows block diagrams each illustrating a configuration of a semiconductor device that can be used for the authentication system of one embodiment of the present invention.

Note that in this specification, an integer variable of 1 or more is sometimes used in reference numerals. For example, (p) where p is an integer variable of 1 or more is sometimes used in part of a reference numeral that specifies any of p components at a maximum. For another example, (m,n) where m and n are each an integer variable of 1 or more is sometimes used in part of a reference numeral that specifies any of m×n components at a maximum.

<Structure Example 1 of Authentication System>

The authentication system described in this embodiment includes an arithmetic device 610 and an input/output device 620 (see FIG. 1A).

<<Arithmetic Device 610>>

The arithmetic device 610 supplies control data CI1 and control data CI2. The arithmetic device 610 is supplied with a sensor signal DS.

<<Input/output device 620>>

The input/output device 620 includes an electric lock 670 and a reading portion 660.

<<Electric Lock 670>>

The electric lock 670 is unlocked on the basis of the control data Cl2.

<<Reading Portion 660>>>

The reading portion 660 is supplied with the first control data CI1 and supplies the sensor signal DS. In addition, the reading portion 660 includes light-emitting elements 40 and a pixel array 151 (see FIG. 1B).

Any of the semiconductor devices described in Embodiment 2 can be used for the reading portion 660, for example.

<<Light-Emitting Element 40>>

Figure 1C:
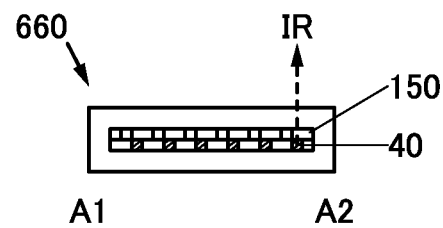
Figure 1D:
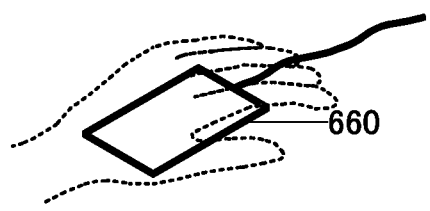
Figure 1E:
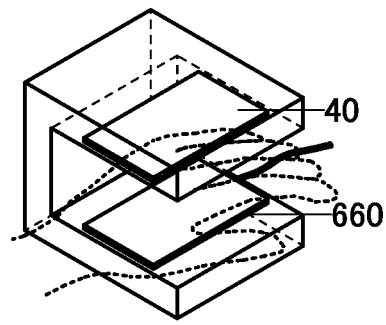

The light-emitting element 40 emits light IR including infrared rays (see FIG. 1C).

<<Pixel Array 151>>

Figure 13A:
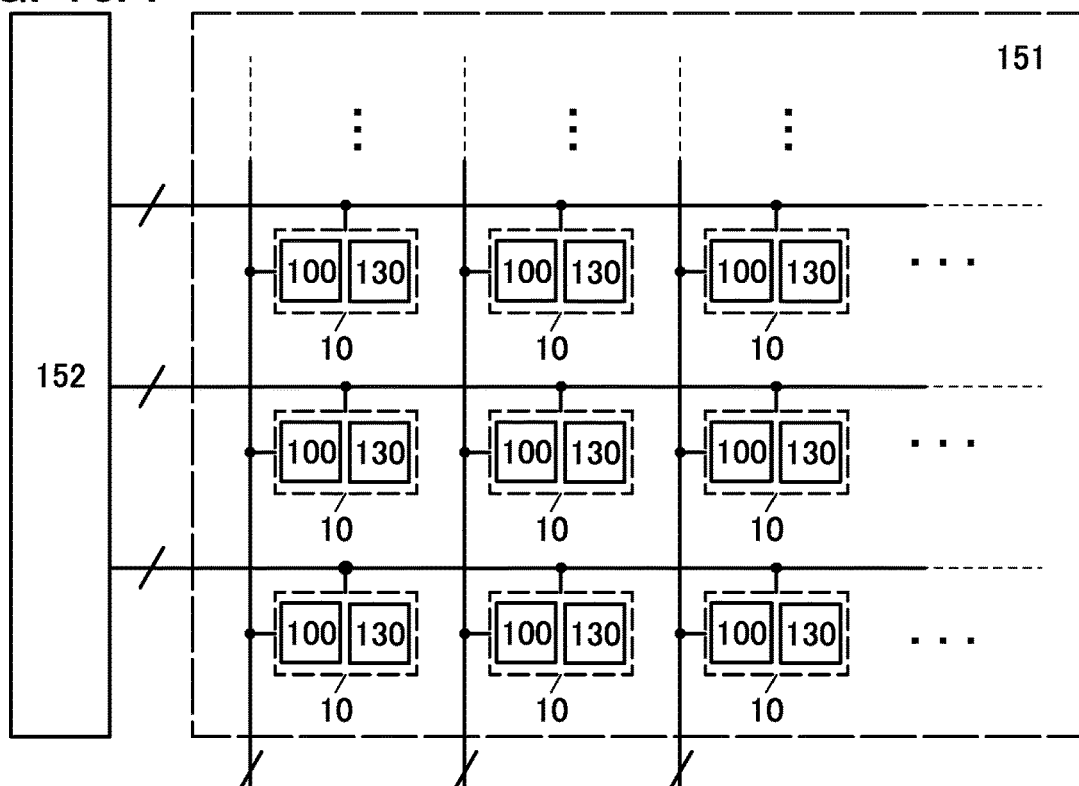
FIG. 13A and FIG. 13B are diagrams each illustrating a configuration example of a semiconductor device.

The pixel array 151 includes pixels 10 (see FIG. 13A).

<<Pixel 10>>

The pixels 10 each include an imaging circuit 100 and a photoelectric conversion element 12 (see FIG. 12).

The imaging circuit 100 is electrically connected to the photoelectric conversion element 12, and the imaging circuit 100 includes a transistor.

The transistor includes an oxide semiconductor film (see FIG. 11).

An oxide semiconductor film with a low carrier concentration is preferably used for a transistor of one embodiment of the present invention. In the case where the carrier concentration of an oxide semiconductor film is lowered, the impurity concentration in the oxide semiconductor film is lowered to decrease the density of defect states. In this specification and the like, a state with a low impurity concentration and a low density of defect states is referred to as a highly purified intrinsic or substantially highly purified intrinsic state. Examples of the impurities in an oxide semiconductor film include hydrogen, nitrogen, alkali metal, alkaline earth metal, iron, nickel, and silicon.

In particular, hydrogen contained in the oxide semiconductor film reacts with oxygen bonded to a metal atom to be water, and thus sometimes forms an oxygen vacancy in the oxide semiconductor film. If the channel formation region in the oxide semiconductor film includes oxygen vacancies, the transistor sometimes has normally-on characteristics. In some cases, a defect that is an oxygen vacancy into which hydrogen has entered functions as a donor and generates an electron serving as a carrier. In other cases, bonding of part of hydrogen to oxygen bonded to a metal atom generates an electron serving as a carrier. Thus, a transistor including an oxide semiconductor film which contains a large amount of hydrogen is likely to be normally on.

A defect that is an oxygen vacancy into which hydrogen has entered can function as a donor of the oxide semiconductor film. However, it is difficult to evaluate the defects quantitatively. Thus, the oxide semiconductor film is sometimes evaluated by not its donor concentration but its carrier concentration. Therefore, in this specification and the like, the carrier concentration assuming the state where an electric field is not applied is sometimes used, instead of the donor concentration, as the parameter of the oxide semiconductor film. That is, "carrier concentration" in this specification and the like may be replaced with "donor concentration".

Thus, in the case where an oxide semiconductor film is used for the transistor, hydrogen in the oxide semiconductor film is preferably reduced as much as possible. Specifically, the hydrogen concentration of the oxide semiconductor film, which is measured by secondary ion mass spectrometry (SIMS), is lower than $1\times10^{20}$ atoms/cm$^3$, preferably lower than $1\times10^{19}$ atoms/cm$^3$, more preferably lower than $5\times10^{18}$ atoms/cm$^3$, still more preferably lower than $1\times10^{18}$ atoms/cm$^3$. When an oxide semiconductor film with sufficiently reduced impurities such as hydrogen is used for a channel formation region of a transistor, stable electrical characteristics can be given.

The carrier concentration of an oxide semiconductor film functioning as a channel formation region is preferably lower than or equal to $1\times10^{18}$ cm$^{-3}$, further preferably lower than $1\times10^{17}$ cm$^{-3}$, still further preferably lower than $1\times10^{16}$ cm$^{-3}$, yet further preferably lower than $1\times10^{13}$ cm$^{-3}$, and yet still further preferably lower than $1\times10^{12}$ cm$^{-3}$. The minimum carrier density of an oxide semiconductor film at a channel formation region is not limited and can be $1\times10^{-9}$ cm$^{-3}$, for example.

<<Photoelectric Conversion Element 12>>

The photoelectric conversion element 12 includes an organic semiconductor film (see FIG. 11).

Thus, an image of a physical feature can be taken, for example. Alternatively, an image of a vein spread or a vein arrangement pattern can be taken, for example. Alternatively, data included in a physical feature can be extracted. Alternatively, the security level can be increased. As a result, a novel authentication system that is highly convenient or reliable can be provided.

<<Structure Example 2 of Arithmetic Device 610>>

The arithmetic device 610 also includes an arithmetic portion 611 and a memory portion 612 (see FIG. 1A).

The memory portion 612 stores a program and a database DB1.

The arithmetic portion 611 extracts a feature value from the sensor signal DS on the basis of the program, and the arithmetic portion 611 examines the feature value using the database DB1. In addition, the arithmetic portion 611 supplies the control data Cl2 on the basis of the examination result.

In this manner, an individual having a predetermined physical feature can be authenticated, for example. Alternatively, the security level can be increased. As a result, a novel authentication system that is highly convenient or reliable can be provided.

<<Structure Example 2 of Memory Portion 612>>

The memory portion 612 also stores a database DB2.

The arithmetic portion 611 records the unlocking history in the database DB2 on the basis of the examination result.

Accordingly, the unlocking history can be recorded. Furthermore, the unlocking history can be recorded in association with an individual having a predetermined physical feature. Alternatively, the security level can be increased. As a result, a novel authentication system that is highly convenient or reliable can be provided.

<<Program>>

A program of one embodiment of the present invention includes a first step to a seventh step (see FIG. 2).

[First Step]

In the first step, imaging is performed to obtain a sensor signal DS (see (S1) in FIG. 2). Specifically, the arithmetic device 610 of the authentication system supplies the control signal CI1 (see FIG. 1A). Then, the light-emitting element 40 of the reading portion 660 emits the light IR including infrared rays on the basis of the control signal CI1, and imaging is performed using the pixel array 151. Note that the reading portion 660 supplies the sensor signal DS. Thus, the arithmetic device 610 can obtain the sensor signal DS.

[Second Step]

In the second step, the program proceeds to the third step in the case where a change exceeding a predetermined level is observed in the sensor signal DS, and the program proceeds to the first step in the case where only a change less than or equal to the predetermined level is observed (see (S2) in FIG. 2). For example, when an object that partly blocks or reflects the light IR is proximate to the reading portion 660, the sensor signal DS changes (see FIG. 1D or FIG. 1E). Thus, the authentication system can recognize that a subject is near the reading portion 660.

[Third Step]

In the third step, imaging is performed to obtain a sensor signal DS (see (S3) in FIG. 2). Specifically, the arithmetic device 610 of the authentication system supplies the control signal CI1 (see FIG. 1A). The light-emitting element 40 of the reading portion 660 emits the light IR including infrared rays on the basis of the control signal CI1, and imaging is performed using the pixel array 151. Note that the reading portion 660 supplies the sensor signal DS. Thus, the arithmetic device 610 can obtain the sensor signal DS.

[Fourth Step]

In the fourth step, a feature value is extracted from the sensor signal DS (see (S4) in FIG. 2). For example, a feature value derived from a vein spread or a vein arrangement pattern is extracted from the sensor signal DS.

[Fifth Step]

In the fifth step, the feature value is examined using the database DB1, and the program proceeds to the sixth step in the case where the database DB1 includes data matching the feature value. In the case where the database DB1 includes no data matching the feature value, the program proceeds to the first step (see (S5) in FIG. 2).

[Sixth Step]

In the sixth step, the control data CI2 is supplied to unlock the electric lock 670 (see (S6) in FIG. 2).

[Seventh Step]

In the seventh step, the unlocking history is recorded in the database DB2 (see (S7) in FIG. 2).

Thus, the unlocking history can be recorded in the second database DB2. Furthermore, the unlocking history can be recorded in association with an individual having a predetermined physical feature. Alternatively, the security level can be increased. As a result, a novel method for recording unlocking history, which is highly convenient or reliable, can be provided.

Note that this embodiment can be combined with any of the other embodiments in this specification as appropriate.

Embodiment 2

In this embodiment, a semiconductor device that can be used for the authentication system of one embodiment of the present invention and a fabrication method thereof will be described with reference to drawings.

First, a photoelectric conversion element is formed over a substrate, and an opening portion is also provided in the substrate. Next, a conductive layer is formed to be embedded in the opening portion. Then, a transistor is formed over the substrate. For example, a first transistor in which one of a source and a drain is electrically connected to one electrode of the photoelectric conversion element and a second transistor in which one of a source and a drain is electrically connected to the conductive layer are formed.

Next, the back surface of the substrate over which the transistors are formed is polished to expose the conductive layer. After that, a light-emitting element including a pixel electrode, a light-emitting layer, and a common electrode is formed so that the conductive layer and the pixel electrode are electrically connected to each other. The above is the fabrication method of the semiconductor device that can be used for the authentication system of one embodiment of the present invention.

In the semiconductor device that can be used for the authentication system of one embodiment of the present invention, light emitted from the light-emitting element and reflected by a subject is detected by the photoelectric conversion element. The semiconductor device that can be used for the authentication system of one embodiment of the present invention can have a function of performing biometric authentication such as fingerprint authentication or vein authentication by using, for example, an element emitting infrared light as the light-emitting element. Alternatively, the semiconductor device can have a function of performing failure analysis on an industrial product, for example.

Furthermore, the semiconductor device that can be used for the authentication system of one embodiment of the present invention can have a function of displaying an image by using an element emitting visible light as the light-emitting element. Thus, with the use of an element emitting both infrared light and visible light as the light-emitting element, an image can be displayed while the biometric authentication, the failure analysis, or the like is performed. For example, an authentication result can be displayed. Note that even in the case where an element emitting visible light is used as the light-emitting element, the biometric authentication, the failure analysis, or the like can be performed by detecting the visible light, which is emitted from the light-emitting element and reflected by a subject, using the photoelectric conversion element.

In this specification and the like, infrared light refers to light with a wavelength greater than or equal to 0.7 μm and less than or equal to 1000 μm, for example. In addition, near-infrared light that is light with a wavelength of greater than or equal to 0.7 μm and less than or equal to 2.5 μm might be simply referred to as infrared light, for example.

In the semiconductor device that can be used for the authentication system of one embodiment of the present invention, the light-emitting element and the photoelectric conversion element are formed over a layer where transistors, wirings electrically connected to the transistors, and the like are formed. Accordingly, light emitted from the light-emitting element can be inhibited from being blocked by the wirings and the like, so that the semiconductor device that can be used for the authentication system of one embodiment of the present invention can emit high-luminance light and the semiconductor device that can be used for the authentication system of one embodiment of the present invention can have reduced power consumption. Furthermore, light incident on the semiconductor device can be inhibited from being blocked by the wirings and the like, so that the semiconductor device that can be used for the authentication system of one embodiment of the present invention can have higher light detection sensitivity.

<Cross-Sectional Structure Example 1 of Pixel>

Figure 3:
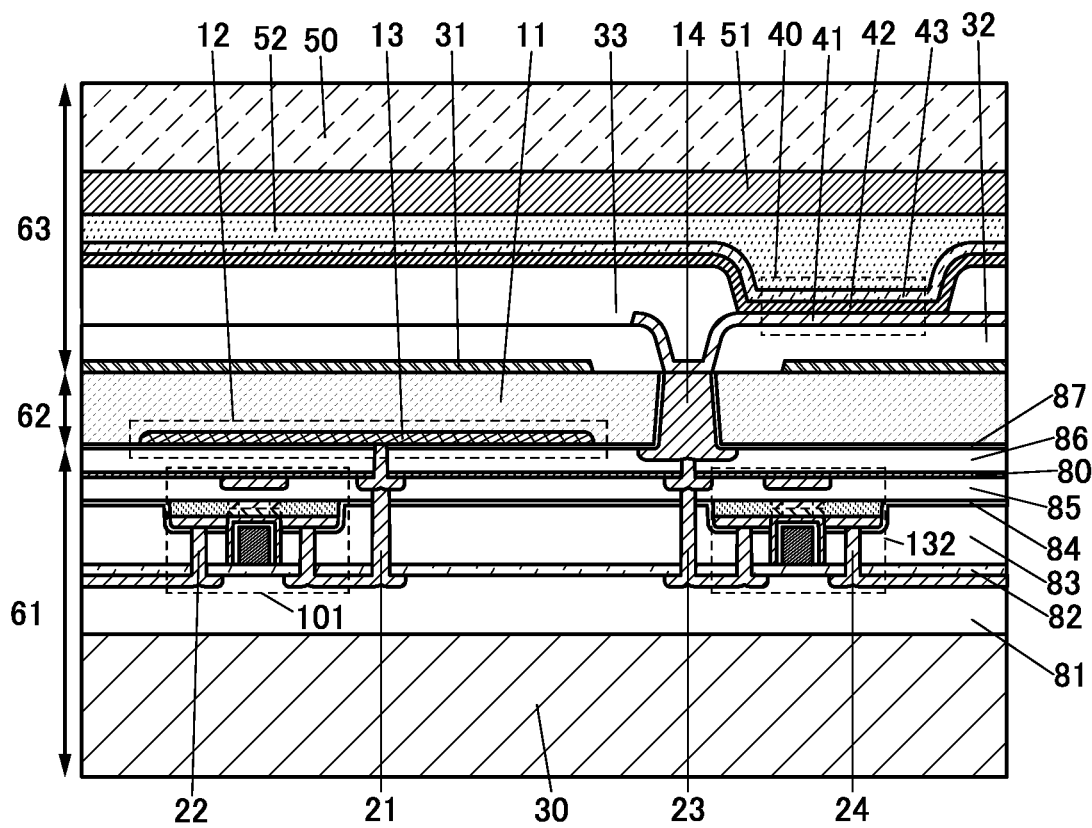
FIG. 3 is a diagram illustrating a structure example of a semiconductor device.

FIG. 3 is a cross-sectional view illustrating a structure example of the pixel 10, which is a pixel included in the semiconductor device of one embodiment of the present invention. The pixel 10 includes a transistor 101, a transistor 132, the photoelectric conversion element 12, the light-emitting element 40, and the like between a substrate 30 and a substrate 50. Here, transistors using a metal oxide in their channel formation regions (hereinafter, OS transistors) can be used as the transistor 101 and the transistor 132, for example.

As illustrated in FIG. 3, the pixel 10 can have a stacked-layer structure of a layer 61, a layer 62, and a layer 63. In the layer 61, the substrate 30, an insulating layer 81, an insulating layer 82, the transistor 101, the transistor 132, an insulating layer 80, and an insulating layer 86 are provided. The transistor 101 and the transistor 132 are provided between the insulating layer 82 and the insulating layer 80. An insulating layer 84 and an insulating layer 85 are provided to cover channel formation regions, source regions, and drain regions of the transistor 101 and the transistor 132. An insulating layer 83 is provided between the insulating layer 82 and the insulating layer 84.

A conductive layer 21 is provided to be electrically connected to one of the source and the drain of the transistor 101, and a conductive layer 22 is provided to be electrically connected to the other of the source and the drain of the transistor 101. A conductive layer 23 is provided to be electrically connected to one of the source and the drain of the transistor 132, and a conductive layer 24 is provided to be electrically connected to the other of the source and the drain of the transistor 132. Note that the conductive layer 21 to the conductive layer 24 may each be referred to as a wiring. Similarly, other conductive layers provided in the semiconductor device of one embodiment of the present invention may each be referred to as a wiring.

As the substrate 30, a silicon substrate, a glass substrate, a ceramics substrate, a resin substrate, or the like can be used. Note that a substrate containing a material similar to that for the substrate 30 can be used as other substrates provided in the semiconductor device of one embodiment of the present invention.

It is preferable that at least one of the insulating layer 80 to the insulating layer 86 be formed using a material through which impurities such as water and hydrogen are less likely to diffuse. This enables the insulating layers to function as barrier films, so that entry of impurities into the transistor 101, the transistor 132, and the like can be inhibited efficiently. Consequently, the reliability of the semiconductor device of one embodiment of the present invention can be increased.

As the transistors provided in the layer 61, such as the transistor 101 and the transistor 132, thin-film transistors such as OS transistors are preferably used. In this case, elements such as the transistors provided in the layer 61 can be isolated from each other without provision of an element isolation layer such as a field oxide film. Thus, the semiconductor device of one embodiment of the present invention can be fabricated by a simple method.

In the layer 62, a substrate 11 and the photoelectric conversion element 12 are provided. The substrate 11 can be a silicon substrate, for example. The silicon substrate can include a single crystal with a crystal orientation of (100), for example. The thickness of the substrate 11 is preferably greater than or equal to 2 μm and less than or equal to 20 μm.

In this specification and the like, the surface of the substrate 11 on the layer 61 side refers to a front surface, and the surface on the layer 63 side refers to a back surface.

The photoelectric conversion element 12 can be provided over the substrate 11, and can be a pn-junction photodiode or a pin-junction photodiode, for example. The photoelectric conversion element 12 can be formed by, for example, provision of a low-resistance region 13 in the substrate 11. In the case where the substrate 11 is a p-type substrate, for example, the low-resistance region 13 is made to be an n-type region, whereby a pn-junction photodiode can be formed as the photoelectric conversion element 12. Here, the electric resistance of the substrate 11 is preferably higher than or equal to 8 Ω·cm and lower than or equal to 12 Ω·cm.

In the case where the photoelectric conversion element 12 is formed by provision of the low-resistance region 13 in the substrate 11, one electrode of the photoelectric conversion element 12 can include the low-resistance region 13 and the other electrode of the photoelectric conversion element 12 can include the substrate 11. In the case where the substrate 11 is a p-type substrate and the low-resistance region 13 is an n-type region, for example, an anode of the photoelectric conversion element 12 can include the substrate 11 and a cathode of the photoelectric conversion element 12 can include the low-resistance region 13.

The low-resistance region 13 is electrically connected to the conductive layer 21. Thus, one electrode of the photoelectric conversion element 12 is electrically connected to one of the source and the drain of the transistor 101 through the conductive layer 21. Therefore, the transistor 101 can have a function of controlling the operation of the photoelectric conversion element 12.

An opening portion is provided in the substrate 11 and an insulating layer 87 is provided to cover a side surface of the opening portion. A conductive layer 14 is provided in the opening portion whose side surface is covered with the insulating layer 87, and the conductive layer 14 is electrically connected to the conductive layer 23.

In the case where an OS transistor is used as the transistors provided in the layer 61, such as the transistor 101 and the transistor 132, hydrogen in the insulating layer provided in the vicinity of the channel formation region of the transistor is a factor of generating carriers in a metal oxide layer. For this reason, hydrogen in the insulating layer provided in the vicinity of the channel formation region of the OS transistor is preferably as little as possible. Meanwhile, in the case where a silicon substrate is used as the substrate 11, hydrogen in the insulating layer provided in the vicinity of the photoelectric conversion element 12 terminates a dangling bond of silicon. Thus, hydrogen in the insulating layer provided in the vicinity of the photoelectric conversion element 12 is preferably as much as possible. When the insulating layer 80 is formed using a material that is less likely to transmit hydrogen, hydrogen can be confined to the substrate 11 side and thus entry of hydrogen into the transistor 101, the transistor 132, and the like can be inhibited. Thus, the reliability of the semiconductor device of one embodiment of the present invention can be high compared to the case where the insulating layer 80 is not provided.

Examples of the material that is less likely to transmit hydrogen and can be used for the insulating layer 80 include aluminum oxide, aluminum oxynitride, gallium oxide, gallium oxynitride, yttrium oxide, yttrium oxynitride, hafnium oxide, hafnium oxynitride, and yttria-stabilized zirconia (YSZ).

In the layer 63, a conductive layer 31, an insulating layer 32, the light-emitting element 40, and an insulating layer 33 are provided. The substrate 50 and a filter 51 are also provided in the layer 63. The substrate 50 and the substrate 11 are sealed with a sealing layer 52. An element having a function of emitting white light and infrared light is preferably used as the light-emitting element 40, for example.

The conductive layer 31 is provided to include a region in contact with the substrate 11. Providing the conductive layer 31 can reduce the resistance of the other electrode of the photoelectric conversion element 12.

The insulating layer 32 is provided to cover the conductive layer 31, and the light-emitting element 40 is provided over the insulating layer 32. The light-emitting element 40 has a stacked-layer structure in which a conductive layer 41, an EL layer 42, and a conductive layer 43 are stacked in this order from the insulating layer 32 side. That is, the light-emitting element 40 can be an EL (Electro-Luminescence) element. Using an EL element as the light-emitting element 40 enables the semiconductor device of one embodiment of the present invention to be downsized and thinned, leading to application to a variety of electronic devices and an improvement in portability of the electronic devices.

The conductive layer 41 is electrically connected to the conductive layer 14 through the opening provided in the insulating layer 32. In addition, the insulating layer 33 is provided to cover an end of the conductive layer 41.

For the insulating layer 32 and the insulating layer 33, an oxide insulating film, a nitride insulating film, an oxynitride insulating film, or a nitride oxide insulating film can be used, for example. The insulating layers can each be formed to be a single layer or a stacked layer. Examples of the oxide insulating film include a silicon oxide film, an aluminum oxide film, a gallium oxide film, a germanium oxide film, an yttrium oxide film, a zirconium oxide film, a lanthanum oxide film, a neodymium oxide film, a hafnium oxide film, and a tantalum oxide film. Examples of the nitride insulating film include a silicon nitride film and an aluminum nitride film. Examples of the oxynitride insulating film include a silicon oxynitride film. Examples of the nitride oxide insulating film include a silicon nitride oxide film. Note that other insulating layers included in the semiconductor device of one embodiment of the present invention, such as the insulating layer 81 to the insulating layer 87 and gate insulating layers of the transistor 101 and the transistor 132, can be insulating layers containing any of the above materials in some cases.

In this specification and the like, "silicon oxynitride" is a material that contains more oxygen than nitrogen in its composition. Moreover, in this specification and the like, "silicon nitride oxide" is a material that contains more nitrogen than oxygen in its composition.

For the conductive layer 41, a low-resistance conductive film of a metal or the like can be used. For example, the conductive layer 41 can be formed using one or more kinds of metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof. Note that other conductive layers included in the semiconductor device of one embodiment of the present invention, such as the conductive layer 21 to the conductive layer 24, the conductive layer 14, and the source electrodes, the drain electrodes, and the gate electrodes of the transistor 101 and the transistor 132, can be conductive layers containing any of the above materials in some cases.

The conductive layer 41 and the conductive layer 43 have functions of the electrodes of the light-emitting element 40. Thus, it can be said that one electrode of the light-emitting element 40 is electrically connected to one of the source and the drain of the transistor 132 through the conductive layer 14 and the conductive layer 23. Therefore, the transistor 132 can have a function of controlling the operation of the light-emitting element 40. Note that the conductive layer 41 can have a function of a pixel electrode of the light-emitting element 40, for example, and the conductive layer 43 can have a function of a common electrode of the light-emitting element 40, for example.

As the conductive layer 43, a conductive layer having a light-transmitting property can be used. For example, in the case where the light-emitting element 40 has a function of emitting visible light and infrared light, a light-transmitting conductive layer that transmits visible light and infrared light can be used as the conductive layer 43. For example, an indium oxide containing tungsten oxide, an indium zinc oxide containing tungsten oxide, an indium oxide containing titanium oxide, an indium tin oxide (ITO), an indium tin oxide containing titanium oxide, an indium zinc oxide, or an indium tin oxide to which silicon oxide is added can be used. Alternatively, a cadmium tin oxide (CTO) or the like can be used.

The sealing layer 52 has a function of inhibiting entry of oxygen, hydrogen, moisture, carbon dioxide, or the like into the light-emitting element 40. As the sealing layer 52, an ultraviolet curable resin or a thermosetting resin can be used as well as an inert gas such as nitrogen or argon; for example, PVC (polyvinyl chloride), an acrylic resin, polyimide, an epoxy resin, a silicone resin, PVB (polyvinyl butyral), EVA (ethylene vinyl acetate), or the like can be used. A drying agent may be contained in the sealing layer 52.

As part of the sealing layer 52, a protective layer of, for example, silicon nitride, silicon nitride oxide, aluminum oxide, aluminum nitride, aluminum oxynitride, aluminum nitride oxide, or DLC (Diamond Like Carbon) may be provided.

The filter 51 is provided to include a region overlapping with the photoelectric conversion element 12 and the light-emitting element 40, with the sealing layer 52 therebetween. The filter 51 has a function of absorbing light with a specific wavelength. For example, the filter 51 has a function of absorbing light except red light. In this case, when white light is emitted from the light-emitting element 40, red light is emitted to the outside of the pixel 10 through the substrate 50 and the like. Alternatively, the filter 51 has a function of absorbing light except green light, for example. In this case, when white light is emitted from the light-emitting element 40, green light is emitted to the outside of the pixel 10 through the substrate 50 and the like. Alternatively, the filter 51 has a function of absorbing light except blue light, for example. In this case, when white light is emitted from the light-emitting element 40, blue light is emitted to the outside of the pixel 10 through the substrate 50 and the like.

Alternatively, the filter 51 can have a structure with a function of absorbing light except infrared light. For example, the filter 51 has a function of absorbing visible light. In this case, when white light and infrared light are emitted from the light-emitting element 40, infrared light is emitted to the outside of the pixel 10 through the substrate 50 and the like.

The pixel 10 includes the photoelectric conversion element 12 and the light-emitting element 40. Thus, light emitted from the light-emitting element 40 to the outside of the pixel 10 through the substrate 50 and the like, hit a subject, and reflected thereby can be detected by the photoelectric conversion element 12. Accordingly, using an element emitting infrared light as the light-emitting element 40, for example, enables the semiconductor device of one embodiment of the present invention to have a function of detecting an object. For example, vein authentication can be performed by holding a palm over the semiconductor device of one embodiment of the present invention, and fingerprint authentication can be performed by holding a finger thereover. That is, the semiconductor device of one embodiment of the present invention can have a function of performing biometric authentication. In addition, the semiconductor device of one embodiment of the present invention can be used for non-destructive inspection such as foreign substance inspection of a food and failure analysis of an industrial product.

When the filter 51 is provided to include a region overlapping not only with the light-emitting element 40 but also with the photoelectric conversion element 12, light with a wavelength other than the wavelength of light emitted from the light-emitting element 40 to the outside of the pixel 10 through the substrate 50 can be inhibited from being incident on the photoelectric conversion element 12. This can increase the detection accuracy of the photoelectric conversion element 12, leading to higher reliability of the semiconductor device of one embodiment of the present invention.

When the light-emitting element 40 has a function of emitting visible light such as white light, the semiconductor device of one embodiment of the present invention can have a function of displaying an image. For example, an image corresponding to imaging data obtained by the photoelectric conversion element 12 can be displayed using the light-emitting element 40. Alternatively, information obtained from the imaging data obtained by the photoelectric conversion element 12, such as an authentication result, can be displayed. Alternatively, an image corresponding to image data supplied from the outside of the pixel 10 can be displayed. For example, an image corresponding to image data obtained through the Internet can be displayed.

As described above, the semiconductor device of one embodiment of the present invention can display an image while performing the biometric authentication, the failure analysis, or the like by using an element emitting both infrared light and visible light as the light-emitting element 40. Note that even in the case where an element emitting visible light is used as the light-emitting element 40, the biometric authentication, the failure analysis, or the like can be performed by detecting visible light, which is emitted from the light-emitting element 40 to the outside of the pixel 10 through the substrate 50 and the like and reflected by a subject, using the photoelectric conversion element 12.

Thus, the semiconductor device of one embodiment of the present invention can be regarded as a semiconductor device including an imaging device provided with the photoelectric conversion element 12 and a display device provided with the light-emitting element 40.

Note that the substrate 50 is a substrate having a light-transmitting property, such as a glass substrate. Thus, light emitted from the light-emitting element 40 and light incident on the photoelectric conversion element 12 can be inhibited from being blocked by the substrate 50. Accordingly, the semiconductor device of one embodiment of the present invention can emit high-luminance light and the semiconductor of one embodiment of the present invention can have reduced power consumption. Furthermore, the semiconductor device of one embodiment of the present invention can have higher light detection sensitivity.

Like the conductive layer 43, the conductive layer 31 can be formed using a conductive layer having a light-transmitting property. For example, a light-transmitting conductive layer that transmits visible light and infrared light can be used. In this case, light incident on the photoelectric conversion element 12 can be inhibited from being blocked by the conductive layer 31, leading to higher light detection sensitivity of the semiconductor device of one embodiment of the present invention. Note that the conductive layer 31 can contain a material that can be used for the conductive layer 43, for example.

Note that the EL layer 42 overlapping with the conductive layer 41 and the conductive layer 43 can emit light, whereas the EL layer 42 overlapping with the conductive layer 43 but not overlapping with the conductive layer 41 cannot emit light. Since the EL layer 42 is an extremely thin film, absorption of visible light and infrared light can be ignored. Accordingly, the EL layer 42 and the conductive layer 43 can be provided to overlap with the photoelectric conversion element 12.

As illustrated in FIG. 3, in the pixel 10, the photoelectric conversion element 12 and the light-emitting element 40 are formed over the layer 61 where the transistors, the wirings electrically connected to the transistors, and the like are formed. Accordingly, light emitted from the light-emitting element 40 can be inhibited from being blocked by the wirings and the like, so that the semiconductor device of one embodiment of the present invention can emit high-luminance light and the semiconductor device of one embodiment of the present invention can have reduced power consumption. Furthermore, light incident on the semiconductor device can be inhibited from being blocked by the wirings and the like, so that the semiconductor device of one embodiment of the present invention can have higher light detection sensitivity.

Figure 4A:
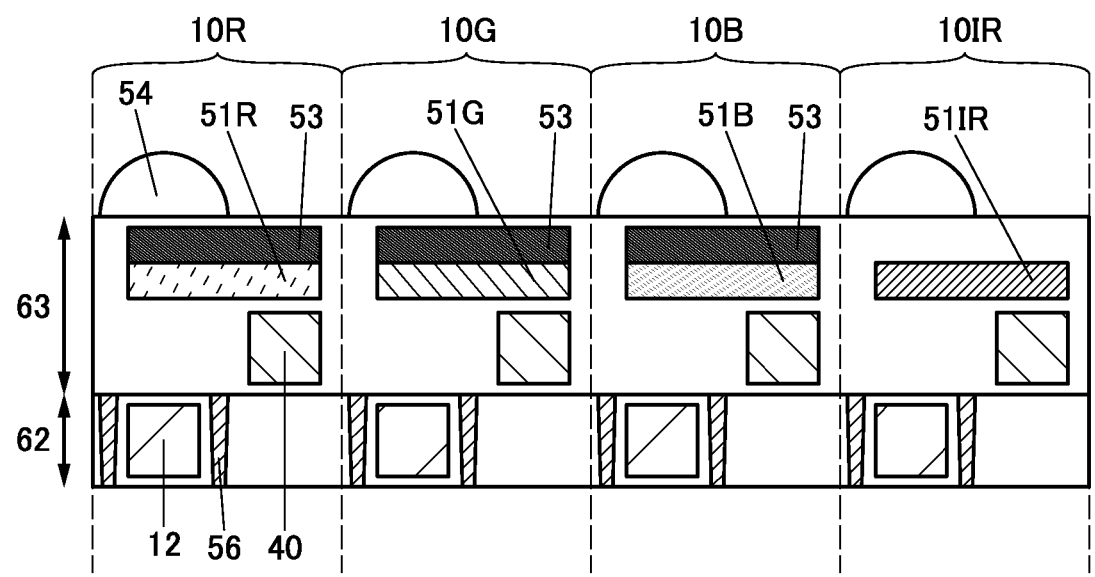
FIG. 4A and FIG. 4B are diagrams each illustrating a structure example of a semiconductor device.

FIG. 4A is a diagram illustrating a structure example of the semiconductor device of one embodiment of the present invention. FIG. 4A illustrates structure examples of a pixel 10R, a pixel 10G, a pixel 10B, and a pixel 10IR as the pixel 10.

The structure illustrated in FIG. 3 can be used for each of the pixel 10R, the pixel 10G, the pixel 10B, and the pixel 10IR. Although the layer 61 is omitted in FIG. 4A, the pixel 10R, the pixel 10G, the pixel 10B, and the pixel 10IR each actually include the layer 61.

The semiconductor device of one embodiment of the present invention can have a structure in which side surfaces of the photoelectric conversion element 12 having the structure illustrated in FIG. 4A are surrounded by a light control layer 56. The light control layer 56 has a function of an element isolation layer between adjacent photoelectric conversion elements 12. Light incident from the light-receiving surface toward the side surface of the photoelectric conversion element 12 can be reflected or attenuated by the light control layer 56. Accordingly, the light can be prevented from entering an adjacent photoelectric conversion element 12. This can increase the detection accuracy of the photoelectric conversion element 12, leading to higher reliability of the semiconductor device of one embodiment of the present invention. Note that the light control layer 56 is not necessarily provided.

A material having a lower refractive index than silicon is preferably used for the light control layer 56. For example, an insulator such as aluminum oxide, magnesium oxide, silicon oxide, silicon oxynitride, silicon nitride oxide, silicon nitride, gallium oxide, germanium oxide, yttrium oxide, zirconium oxide, lanthanum oxide, neodymium oxide, hafnium oxide, or tantalum oxide can be used. Alternatively, an organic material such as an acrylic resin or polyimide may be used. The use of a material having a lower refractive index than silicon facilitates total reflection of light incident on the side surface of the photoelectric conversion element 12. Furthermore, a gas such as air, nitrogen, oxygen, argon, or helium can be used instead of the above material. In this case, the gas may have a pressure lower than an atmospheric pressure.

A material that is likely to absorb light may be used for the light control layer 56. For example, it is possible to use a resin to which a material such as a carbon-based black pigment such as carbon black, a titanium-based black pigment such as titanium black, an oxide of iron, a composite oxide of copper and chromium, or a composite oxide of copper, chromium, and zinc is added.

As described above, the light-emitting element 40 provided in the layer 63 can have a function of emitting white light and infrared light, for example. In the layer 63 included in the pixel 10R, a filter 51R can be provided to include a region overlapping with the photoelectric conversion element 12 and the light-emitting element 40. The filter 51R has a function of transmitting red light, for example. Thus, the pixel 10R can have functions of emitting red light and detecting red light by the photoelectric conversion element 12.

In the layer 63 included in the pixel 10G, a filter 51G can be provided to include a region overlapping with the photoelectric conversion element 12 and the light-emitting element 40. The filter 51G has a function of transmitting green light, for example. Thus, the pixel 10G can have functions of emitting green light and detecting green light by the photoelectric conversion element 12.

In the layer 63 included in the pixel 10B, a filter 51B can be provided to include a region overlapping with the photoelectric conversion element 12 and the light-emitting element 40. The filter 51B has a function of transmitting blue light, for example. Thus, the pixel 10B can have functions of emitting blue light and detecting blue light by the photoelectric conversion element 12.

In the layer 63 included in the pixel 10IR, a filter 51IR can be provided to include a region overlapping with the photoelectric conversion element 12 and the light-emitting element 40. The filter 51IR has functions of transmitting infrared light and absorbing visible light, for example. Thus, the pixel 10B can have functions of emitting infrared light and detecting infrared light by the photoelectric conversion element 12.

The pixel 10R has functions of emitting red light and detecting the light, the pixel 10G has functions of emitting green light and detecting the light, the pixel 10B has functions of emitting blue light and detecting the light, and the pixel 10IR has functions of emitting infrared light and detecting the light; thus, the semiconductor device of one embodiment of the present invention can have functions of displaying a color image and detecting visible light and infrared light. Note that the pixel 10R, the pixel 10G, and the pixel 10B may each have functions of emitting light of yellow, cyan, magenta, or the like and detecting the light.

Here, the pixel 10R, the pixel 10G, the pixel 10B, and the pixel 10IR can each be referred to as a subpixel. In addition, the pixel 10R, the pixel 10G, the pixel 10B, and the pixel 10IR can be regarded as forming one pixel. Note that in this specification and the like, the term "pixel" refers to "subpixel" in some cases. For example, the pixel 10 can be referred to as a subpixel.

In the pixel 10R, a filter 53 can be provided to include a region overlapping with the filter 51R. In the pixel 10G, the filter 53 can be provided to include a region overlapping with the filter 51G. In the pixel 10B, the filter 53 can be provided to include a region overlapping with the filter 51B. The filter 53 has functions of transmitting visible light and absorbing infrared light, for example. That is, the filter 53 can be regarded as an infrared light cut filter.

Providing the filter 53 in the pixel 10R, the pixel 10G, and the pixel 10B inhibits infrared light from being detected by the photoelectric conversion element 12 included in the pixel 10R, the photoelectric conversion element 12 included in the pixel 10G, and the photoelectric conversion element 12 included in the pixel 10B, even in the case where all the light-emitting elements 40 have a function of emitting infrared light, for example. This can increase the detection accuracy of the photoelectric conversion element 12, leading to higher reliability of the semiconductor device of one embodiment of the present invention.

Although FIG. 4A illustrates a structure in which the filter 53 is provided over the filter 51R, the filter 51G, and the filter 51B, the filter 53 may be provided below the filter 51R, the filter 51G, and the filter 51B.

A microlens 54 can be provided over the layer 63 to include a region overlapping with the photoelectric conversion element 12. This can increase the light detection sensitivity of the photoelectric conversion element 12.

Figure 4B:
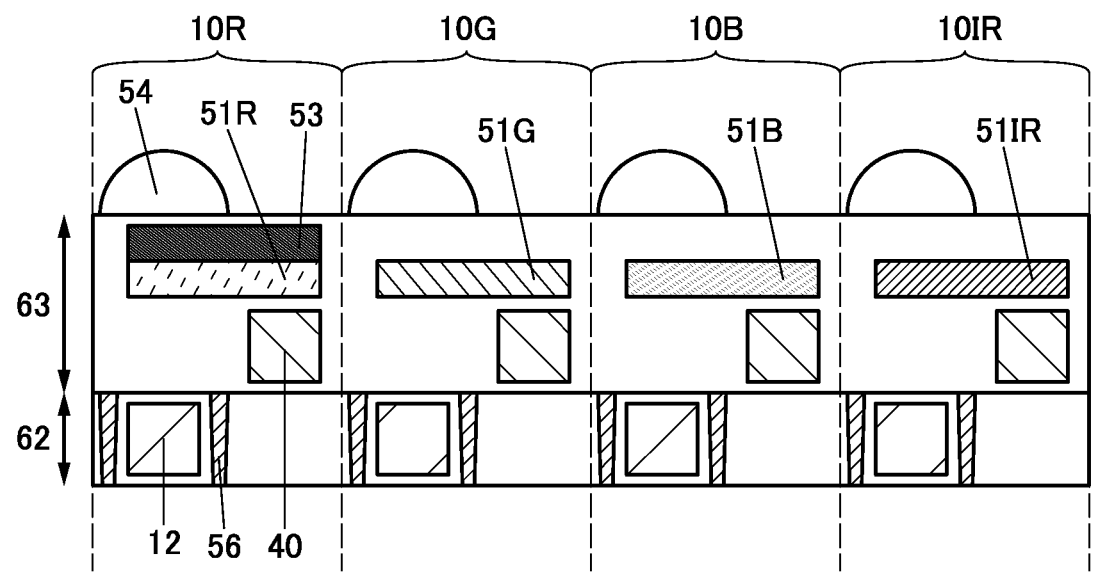

FIG. 4B is a diagram illustrating a structure example of the semiconductor device of one embodiment of the present invention, and is a modification example of the structure illustrated in FIG. 4A. The semiconductor device having the structure illustrated in FIG. 4B is different from the semiconductor device having the structure illustrated in FIG. 4A in that the filter 53 is not provided in the pixel 10G and the pixel 10B.

The filter 51G and the filter 51B each have a function of absorbing red light. Thus, infrared light with a wavelength close to that of red light is also absorbed in some cases. In this case, infrared light can be inhibited from being detected by the photoelectric conversion element 12 provided in the pixel 10G and the photoelectric conversion element 12 provided in the pixel 10B, even when the pixel 10G and the pixel 10B are not provided with the filter 53 having a function of absorbing infrared light. When the semiconductor device of one embodiment of the present invention has the structure illustrated in FIG. 4B, light emitted from the light-emitting element 40 included in the pixel 10G and light emitted from the light-emitting element 40 included in the pixel 10B can be inhibited from being absorbed by the filter 53. Thus, the semiconductor device of one embodiment of the present invention can emit high-luminance light and the semiconductor device of one embodiment of the present invention can have reduced power consumption. Furthermore, the semiconductor device of one embodiment of the present invention can have higher light detection sensitivity.

<Example of Fabrication Method of Pixel>

FIG. 5A, FIG. 5B, FIG. 5C, FIG. 5D, FIG. 6A, FIG. 6B, FIG. 6C, FIG. 7A, and FIG. 7B are diagrams illustrating an example of a fabrication method of the pixel 10 having the structure illustrated in FIG. 3.

Note that thin films that form the light-emitting device (insulating films, semiconductor films, conductive films, and the like) can be formed by a sputtering method, a chemical vapor deposition (CVD) method, a vacuum evaporation method, a pulsed laser deposition (PLD) method, an atomic layer deposition (ALD) method, or the like. Examples of the CVD method include a plasma-enhanced chemical vapor deposition (PECVD) method and a thermal CVD method. In addition, examples of the thermal CVD method include a metal organic chemical vapor deposition (MOCVD) method.

Alternatively, the thin films that form the light-emitting device (the insulating films, the semiconductor films, the conductive films, and the like) can be formed by a method such as spin coating, dipping, spray coating, or a droplet discharging method (e.g., ink jetting and dispensing), a printing method (e.g., screen printing and offset printing), or with an equipment such as a doctor knife, a slit coater, a roll coater, a curtain coater, or a knife coater.

When the thin films that form the light-emitting device are processed, a photolithography method or the like can be used for the processing. Alternatively, the thin films may be processed by a nanoimprinting method, a sandblasting method, a lift-off method, or the like. Island-shaped thin films may be directly formed by a film formation method using a blocking mask such as a metal mask.

There are two typical examples of a photolithography method. In one of the methods, a resist mask is formed over a thin film that is to be processed, and the thin film is processed by etching or the like, so that the resist mask is removed. In the other method, after a photosensitive thin film is formed, exposure and development are performed, so that the thin film is processed into a desired shape.

For light used for exposure in a photolithography method, for example, an i-line (with a wavelength of 365 nm), a g-line (with a wavelength of 436 nm), an h-line (with a wavelength of 405 nm), or light in which these lines are mixed can be used. Besides, ultraviolet light, KrF laser light, ArF laser light, or the like can be used. Furthermore, exposure may be performed by liquid immersion light exposure technique. Furthermore, as the light used for the exposure, extreme ultra-violet (EUV) light or X-rays may be used. Furthermore, instead of the light used for the exposure, an electron beam can also be used. It is preferable to use extreme ultra-violet light, X-rays, or an electron beam because extremely minute processing can be performed. Note that when light exposure is performed by scanning of a beam such as an electron beam, a photomask is unnecessary.

For etching of the thin films, a dry etching method, a wet etching method, a sandblast method, or the like can be used.

Figure 5A:
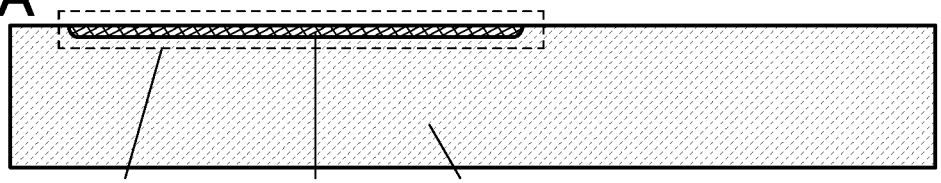
FIG. 5A to FIG. 5D are diagrams illustrating an example of a fabrication method of a semiconductor device.

The example of a fabrication method of the pixel 10 having the structure illustrated in FIG. 3 is described. First, the low-resistance region 13 is formed in the substrate 11 (FIG. 5A). Accordingly, the photoelectric conversion element 12 can be fabricated. The low-resistance region 13 can be formed by impurity addition to the substrate 11. For example, adding a pentavalent element such as phosphorus or arsenic can make the low-resistance region 13 an n-type region, and adding a trivalent element such as boron or aluminum can make the low-resistance region 13 a p-type region. Note that the low-resistance region 13 can be an n-type region in the case where the substrate 11 is a p-type substrate, and the low-resistance region 13 can be a p-type region in the case where the substrate 11 is an n-type substrate.

Example of the method for adding the above impurity include an ion implantation method in which an ionized source gas is subjected to mass separation and then added, an ion doping method in which an ionized source gas is added without mass separation, and a plasma immersion ion implantation method.

Figure 5B:
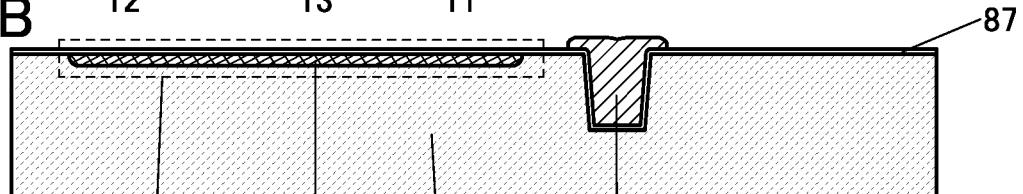

Next, an opening portion is provided in the substrate 11. The opening portion need not penetrate the substrate 11. Then, the insulating layer 87 is provided to cover a side surface of the opening portion, and the conductive layer 14 is formed to fill the opening portion covered with the insulating layer 87 (FIG. 5B).

An SOI substrate may be used as the substrate 11. In this case, an opening portion is provided in the substrate 11 to reach a BOX layer.

Next, the insulating layer 86 is formed over the insulating layer 87 and the conductive layer 14, and the insulating layer 80 is formed over the insulating layer 86. After that, the transistor 101 and the transistor 132 are formed over the insulating layer 80. Note that the insulating layer 85 and the insulating layer 84 are formed to cover the channel formation regions, the source regions, and the drain regions of the transistor 101 and the transistor 132. In addition, the insulating layer 83 is formed over the insulating layer 84. The insulating layer 83 has a function of an interlayer insulating film and is planarized by planarization treatment using a chemical mechanical polishing (CMP) method or the like. Note that the insulating layer 83 is not necessarily planarized. In addition, the layers other than the insulating layer 83 can be subjected to planarization treatment by a CMP method or the like.

The transistor 101 and the transistor 132 can be formed through the same process. In other words, a transistor having a function of controlling the operation of the photoelectric conversion element 12 and a transistor having a function of controlling the operation of the light-emitting element 40 can be fabricated through the same process. Thus, the fabrication process of the semiconductor device of one embodiment of the present invention can be simplified compared to the case where the transistor having a function of controlling the operation of the photoelectric conversion element 12 and the transistor having a function of controlling the operation of the light-emitting element 40 are fabricated through different processes. Therefore, the semiconductor device of one embodiment of the present invention can be inexpensive. Note that a circuit element other than the transistors, such as a capacitor, can be fabricated through the same process as the transistors.

After formation of the transistor 101, the transistor 132, and the like, the insulating layer 82 is formed. Next, opening portions are provided in the insulating layer 80 and the insulating layer 82 to the insulating layer 87, and the conductive layer 21 to the conductive layer 24 are formed to fill the opening portions. Specifically, the conductive layer 21 is formed to be electrically connected to the low-resistance region 13 and one of the source and the drain of the transistor 101, and the conductive layer 22 is formed to be electrically connected to the other of the source and the drain of the transistor 101. The conductive layer 23 is formed to be electrically connected to the conductive layer 14 and one of the source and the drain of the transistor 132, and the conductive layer 24 is formed to be electrically connected to the other of the source and the drain of the transistor 132.

Figure 5C:
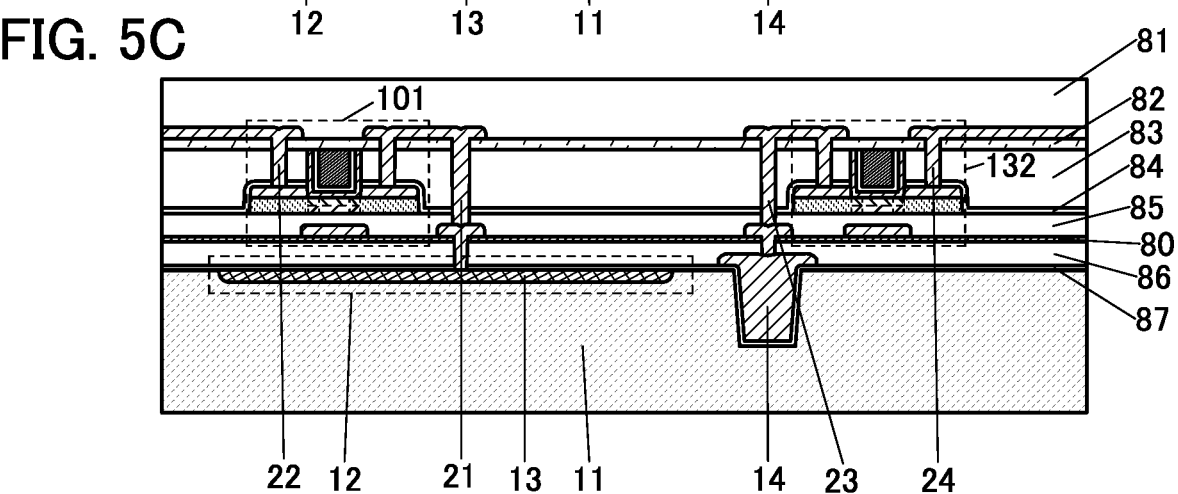
Figure 5D:
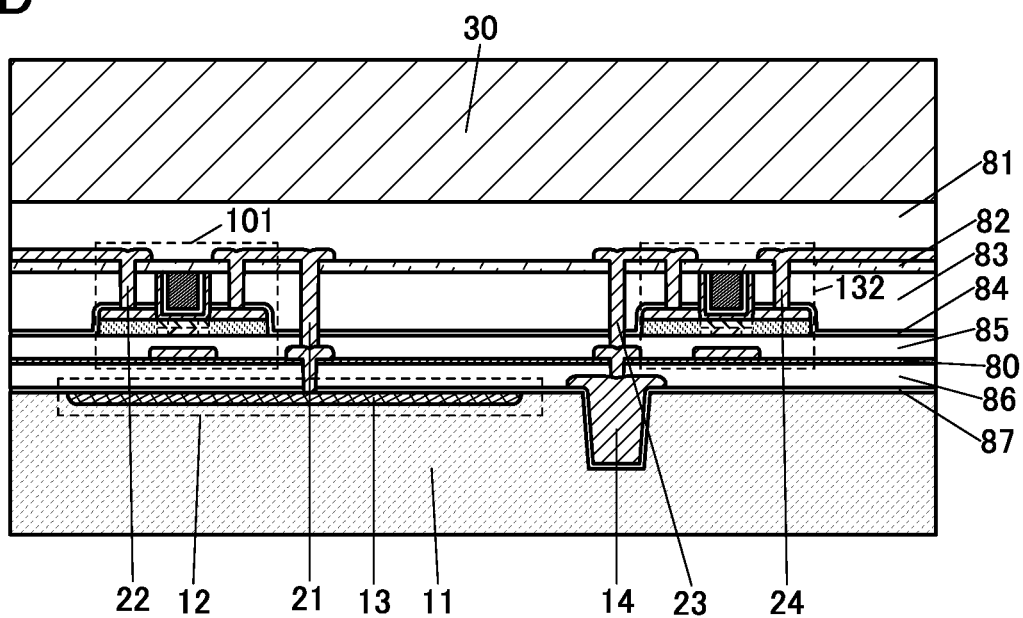

After formation of the conductive layer 21 to the conductive layer 24, the insulating layer 81 is formed over the conductive layer 21 to the conductive layer 24 and the insulating layer 82 (FIG. 5C). After that, the substrate 30 is attached to the insulating layer 81 (FIG. 5D). The insulating layer 81 and the substrate 30 can be attached to each other by compression bonding, for example. Alternatively, the substrate 30 can be attached to the insulating layer 81 with an adhesive layer provided between the insulating layer 81 and the substrate 30. The substrate 30 has a function of a support substrate in the subsequent fabrication steps.

Figure 6A:
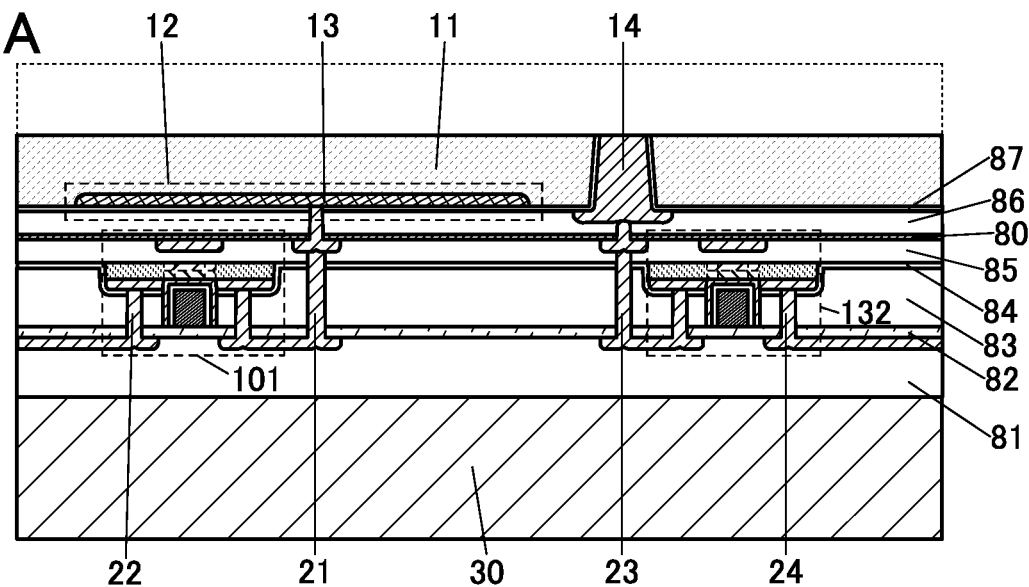
FIG. 6A to FIG. 6C are diagrams illustrating an example of a fabrication method of a semiconductor device.

Next, the back surface of the substrate 11 and the insulating layer 87 are polished to expose the conductive layer 14 (FIG. 6A). The substrate 11 can be polished using a grinder, for example. After the substrate 11 is polished using a grinder, the substrate 11 and the insulating layer 87 are polished by a CMP method, whereby the conductive layer 14 can be exposed. The use of a grinder enables high-speed polishing of the substrate 11. Furthermore, the use of a CMP method enables precise polishing of the substrate 11 and the insulating layer 87, and can increase the planarity of the substrate 11. Note that a portion surrounded by a dotted line in FIG. 6A is the polished portion of the substrate 11.

In the case where the substrate 11 is an SOI substrate, the conductive layer 14 can be exposed by polishing a BOX layer, which is a layer containing a material different from a material contained in the low-resistance region 13. In this manner, the polishing step can be controlled easily.

Figure 6B:
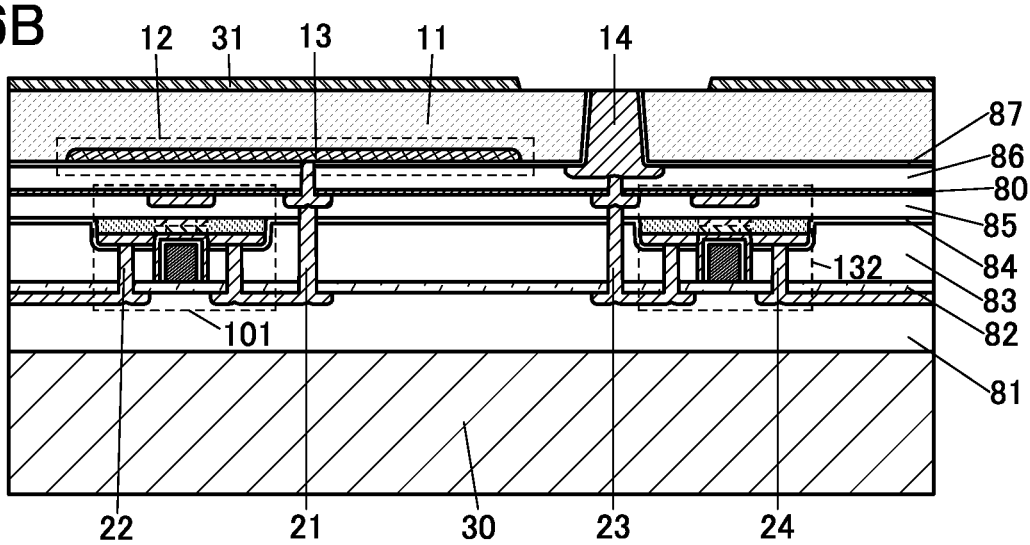

Next, the conductive layer 31 is formed over the substrate 11 (FIG. 6B). Specifically, a conductive film is formed over the substrate 11, the conductive layer 14, and the insulating layer 87, and then patterning is performed by a photolithography method or the like. After that, a portion of the conductive film in contact with the conductive layer 14 is removed by an etching method or the like. In the above manner, the conductive layer 31 can be formed. Note that the conductive layer 31 does not include a region in contact with the insulating layer 87 in FIG. 6B, but may include a region in contact with the insulating layer 87.

Figure 6C:
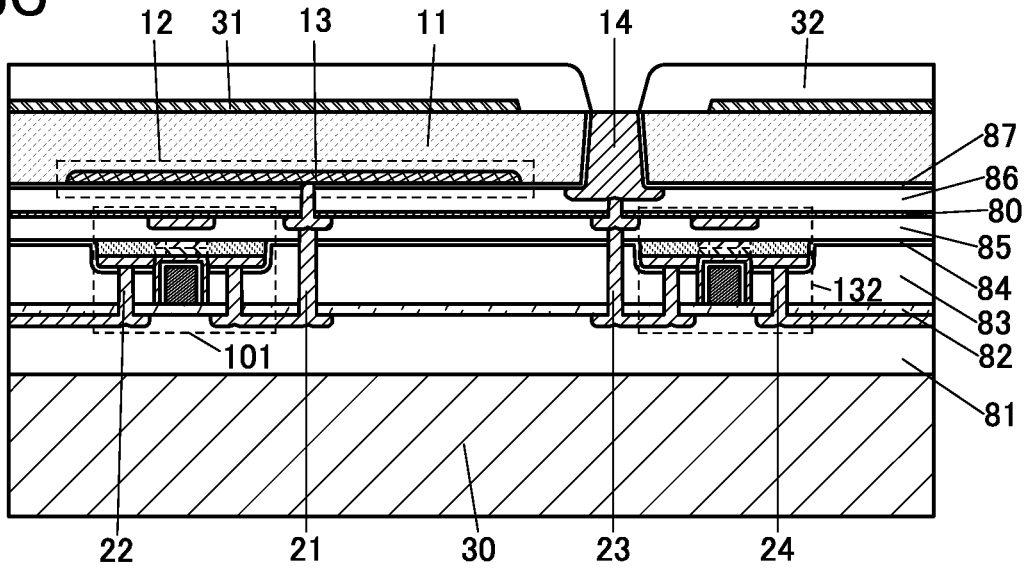

Next, the insulating layer 32 is formed to cover the conductive layer 31 (FIG. 6C). Specifically, an insulating film is formed over the conductive layer 31, the substrate 11, the conductive layer 14, and the insulating layer 87, and an opening portion reaching the conductive layer 14 is formed in the insulating film, whereby the insulating layer 32 can be formed. Note that the insulating layer 32 includes a region in contact with the insulating layer 87 in FIG. 6C, but does not necessarily include a region in contact with the insulating layer 87. In addition, the insulating layer 32 does not include a region in contact with the conductive layer 14 in FIG. 6C, but may include a region in contact with the conductive layer 14.

Figure 7A:
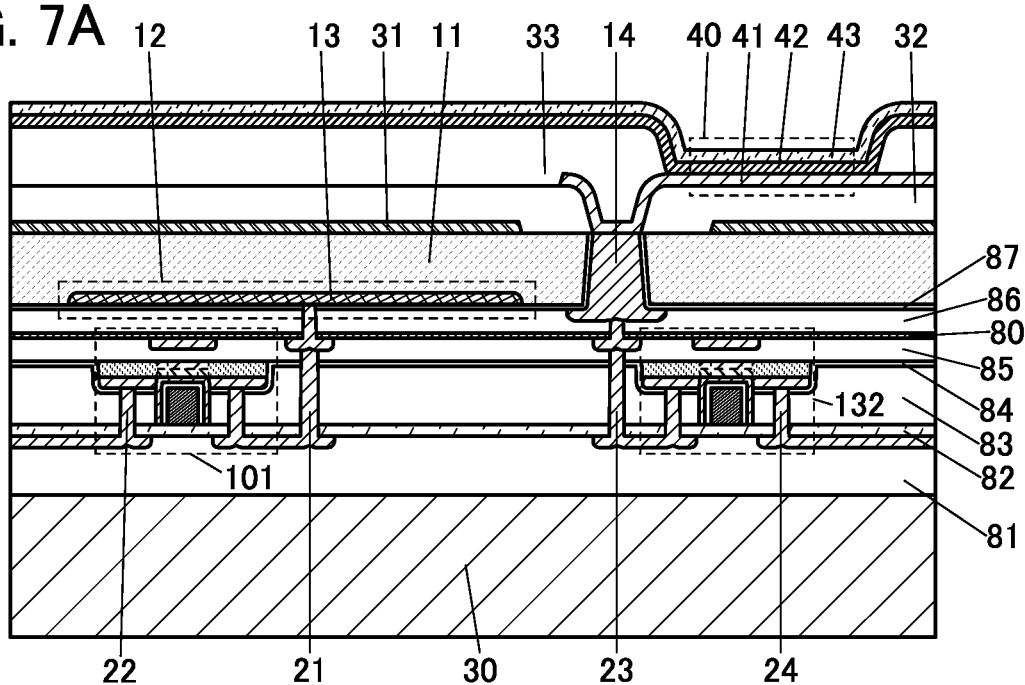
FIG. 7A and FIG. 7B are diagrams illustrating an example of a fabrication method of a semiconductor device.

Next, the conductive layer 41 is formed to be electrically connected to the conductive layer 14. After that, the EL layer 42 is formed to include a region overlapping with the conductive layer 41, and the conductive layer 43 is formed to include a region overlapping with the conductive layer 41 and the EL layer 42 (FIG. 7A). In the above manner, the light-emitting element 40 can be fabricated. Here, the EL layer 42 can be formed by an evaporation method, a coating method, a printing method, a discharge method, or the like.

Figure 7B:
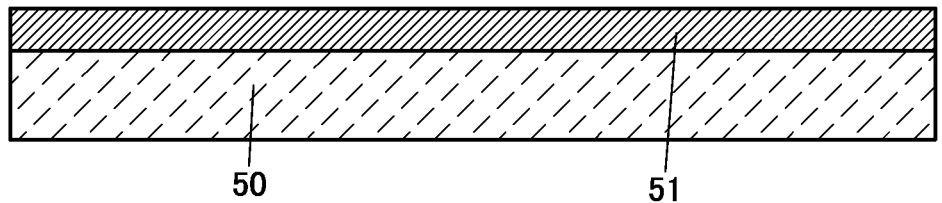

Next, the filter 51 is formed over the substrate 50 (FIG. 7B). Here, the filter 53 having a function of an infrared light cut filter may be formed in addition to the filter 51. Note that the filter 51 and the filter 53 can be formed by an evaporation method (including a vacuum evaporation method), a transfer method, a printing method, an inkjet method, a coating method, or the like.

After that, the substrate 50 and the substrate 11 are sealed with the sealing layer 52. The above is the example of the fabrication method of the pixel 10 having the structure illustrated in FIG. 3.

When the pixel 10 is fabricated by the method illustrated in FIG. 5 to FIG. 7, the photoelectric conversion element 12 and the light-emitting element 40 can be formed over the layer 61, which is a layer where the transistors, the wirings electrically connected to the transistors, and the like are formed. Accordingly, light emitted from the light-emitting element 40 can be inhibited from being blocked by the wirings and the like, so that high-luminance light can be emitted from the semiconductor device of one embodiment of the present invention, and the power consumption of the semiconductor device of one embodiment of the present invention can be reduced. Furthermore, light incident on the semiconductor device can be inhibited from being blocked by the wirings and the like, so that the semiconductor device of one embodiment of the present invention can have higher light detection sensitivity.

<Structure Example of Light-Emitting Element>

FIG. 8A to FIG. 8C are diagrams illustrating structure examples of the light-emitting element 40. FIG. 8A illustrates a structure (a single structure) in which the EL layer 42 is sandwiched between the conductive layer 41 and the conductive layer 43. As described above, the EL layer 42 contains a light-emitting material, for example, a light-emitting material of an organic compound.

FIG. 8B is a diagram illustrating a stacked-layer structure of the EL layer 42. In the light-emitting element 40 having the structure illustrated in FIG. 8B, the conductive layer 41 has a function of an anode and the conductive layer 43 has a function of a cathode.

The EL layer 42 has a structure in which a hole-injection layer 71, a hole-transport layer 72, a light-emitting layer 73, an electron-transport layer 74, and an electron-injection layer 75 are stacked in this order over the conductive layer 41. Note that in the case where the conductive layer 41 has a function of the cathode and the conductive layer 43 has a function of the anode, the stacking order is reversed.

The light-emitting layer 73 contains a light-emitting material and a plurality of materials in appropriate combination, so that fluorescence or phosphorescence of a desired emission color can be obtained. The light-emitting layer 73 may have a stacked-layer structure having different emission colors. In this case, different materials may be used for the light-emitting substance and other substances used in each of the light-emitting layers that are stacked.

For example, when the light-emitting element 40 has a micro optical resonator (microcavity) structure with the conductive layer 41 and the conductive layer 43 illustrated in FIG. 8B respectively serving as a reflective electrode and a semi-transmissive and semi-reflective electrode, light obtained from the light-emitting layer 73 included in the EL layer 42 can be resonated between the electrodes and thus the light emitted through the conductive layer 43 can be intensified.

Note that in the case where the conductive layer 41 of the light-emitting element 40 is a reflective electrode having a stacked-layer structure of a reflective conductive material and a light-transmitting conductive material (transparent conductive film), optical adjustment can be performed by adjusting the thickness of the transparent conductive film.

Specifically, when the wavelength of light obtained from the light-emitting layer 73 is λ, the distance between the conductive layer 41 and the conductive layer 43 is preferably adjusted to around mλ/2 (note that m is a natural number).

To amplify desired light (wavelength: λ) obtained from the light-emitting layer 73, the optical path length from the conductive layer 41 to a region of the light-emitting layer where desired light is obtained (light-emitting region) and the optical path length from the conductive layer 43 to the region of the light-emitting layer 73 where desired light is obtained (light-emitting region) are preferably adjusted to around (2m'+1) λ/4 (note that m' is a natural number). Here, the light-emitting region means a region where holes and electrons are recombined in the light-emitting layer 73.

By such optical adjustment, the spectrum of specific monochromatic light obtained from the light-emitting layer 73 can be narrowed and light emission with high color purity can be obtained.

In the above case, the optical path length between the conductive layer 41 and the conductive layer 43 is, to be exact, the total thickness from a reflective region in the conductive layer 41 to a reflective region in the conductive layer 43. However, it is difficult to precisely determine the reflective region in the conductive layer 41 and the conductive layer 43; hence, it is assumed that the above effect is sufficiently obtained with given positions in the conductive layer 41 and the conductive layer 43 being supposed to be reflective regions. Furthermore, the optical path length between the conductive layer 41 and the light-emitting layer where desired light is obtained is, to be exact, the optical path length between the reflective region in the conductive layer 41 and the light-emitting region where desired light is obtained in the light-emitting layer. However, it is difficult to precisely determine the reflective region in the conductive layer 41 and the light-emitting region in the light-emitting layer where the desired light is obtained; thus, it is assumed that the above effect can be sufficiently obtained with a given position in the conductive layer 41 being supposed to be the reflective region and a given position in the light-emitting layer where the desired light is obtained being supposed to be the light-emitting region.

The light-emitting element 40 illustrated in FIG. 8B has a microcavity structure, so that light (monochromatic light) with different wavelengths can be extracted even if the same EL layer is used. Thus, separate coloring for obtaining different emission colors is not necessary. Therefore, high definition can be easily achieved. In addition, a combination with coloring layers is also possible. Furthermore, the emission intensity of light with a specific wavelength in the front direction can be increased, whereby power consumption can be reduced.

Note that the light-emitting element 40 illustrated in FIG. 8B does not necessarily have a microcavity structure. In this case, light of predetermined colors can be extracted when the light-emitting layer 73 has a structure for emitting white light and infrared light and coloring layers are provided. When the EL layers 42 are formed by separate coloring for obtaining different emission colors, light of predetermined colors can be extracted without providing coloring layers.

At least one of the conductive layer 41 and the conductive layer 43 can be a light-transmitting electrode (e.g., a transparent electrode or a semi-transmissive and semi-reflective electrode). In the case where the light-transmitting electrode is a transparent electrode, the visible light transmittance of the transparent electrode is higher than or equal to 40%. In the case where the light-transmitting electrode is a semi-transmissive and semi-reflective electrode, the visible light reflectance of the semi-transmissive and semi-reflective electrode is higher than or equal to 20% and lower than or equal to 80%, preferably higher than or equal to 40% and lower than or equal to 70%. These electrodes preferably have a resistivity less than or equal to $1\times10^{-2}$ Ωcm.

In the case where the conductive layer 41 or the conductive layer 43 is an electrode having reflectivity (reflective electrode), the visible light reflectance of the electrode having reflectivity is higher than or equal to 40% and lower than or equal to 100%, preferably higher than or equal to 70% and lower than or equal to 100%. This electrode preferably has a resistivity less than or equal to $1\times10^{-2}$ Ωcm.

The structure of the light-emitting element 40 may be the structure illustrated in FIG. 8C. FIG. 8C illustrates a structure (a tandem structure) of the light-emitting element 40 in which three EL layers (an EL layer 42a, an EL layer 42b, and an EL layer 42c) are provided between the conductive layer 41 and the conductive layer 43. Here, a charge generation layer 44a is provided between the EL layer 42a and the EL layer 42b, and a charge generation layer 44b is provided between the EL layer 42b and the EL layer 42c.

The EL layer 42a has a function of emitting blue light, the EL layer 42b has a function of emitting yellow light, and the EL layer 42c has a function of emitting infrared light, for example. Since the complementary color of blue is yellow, the light-emitting element 40 having the structure illustrated in FIG. 8C can have a function of emitting white light and infrared light.

When the light-emitting element 40 has the tandem structure, the current efficiency and the external quantum efficiency of the light-emitting element 40 can be increased. Accordingly, the light-emitting element 40 can emit high-luminance light. Furthermore, the semiconductor device of one embodiment of the present invention can have reduced power consumption. Here, the EL layer 42a, the EL layer 42b, and the EL layer 42c can have a structure similar to that of the EL layer 42 illustrated in FIG. 8B.

The charge generation layer 44a has a function of injecting electrons into one of the EL layer 42a and the EL layer 42b and injecting holes into the other when a voltage is supplied between the conductive layer 41 and the conductive layer 43. The charge generation layer 44b has a function of injecting electrons into one of the EL layer 42b and the EL layer 42c and injecting holes into the other when a voltage is supplied between the conductive layer 41 and the conductive layer 43. Thus, when a voltage is supplied so that the potential of the conductive layer 41 is higher than the potential of the conductive layer 43, electrons are injected from the charge generation layer 44a into the EL layer 42a, and holes are injected from the charge generation layer 44a into the EL layer 42b. In addition, electrons are injected from the charge generation layer 44b into the EL layer 42b, and holes are injected from the charge generation layer 44b into the EL layer 42c.

Note that in terms of light extraction efficiency, the charge generation layer 44 preferably transmits visible light (specifically, the visible light transmittance of the charge generation layer 44 is preferably 40% or higher). The conductivity of the charge generation layer 44 may be lower than the conductivity of the conductive layer 41 or the conductivity of the conductive layer 43.

<Materials for Light-Emitting Element>

Next, materials that can be used for the light-emitting element 40 are described.

<<Conductive Layer 41 and Conductive Layer 43>>

For the conductive layer 41 and the conductive layer 43, materials given below can be used in appropriate combination as long as the functions of the anode and the cathode can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 of the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

<<Hole-Injection Layer 71 and Hole-Transport Layer 72>>

The hole-injection layer 71 is a layer injecting holes from the conductive layer 41 that is the anode or the charge generation layer 44 into the EL layer 42, and is a layer containing a material having a high hole-injection property. Here, the EL layer 42 includes the EL layer 42a, the EL layer 42b, the EL layer 42c, and an EL layer 42(1) to an EL layer 42(n).

Examples of the material having a high hole-injection property include transition metal oxides such as molybdenum oxide, vanadium oxide, ruthenium oxide, tungsten oxide, and manganese oxide. Alternatively, it is possible to use any of the following materials: phthalocyanine-based compounds such as phthalocyanine (abbreviation: H$_2$Pc and copper phthalocyanine (abbreviation: CuPC); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); and the like.

Alternatively, as the material having a high hole-injection property, a composite material containing a hole-transport material and an acceptor material (electron-accepting material) can be used. In this case, the acceptor material extracts electrons from the hole-transport material, so that holes are generated in the hole-injection layer 71 and the holes are injected into the light-emitting layer 73 through the hole-transport layer 72. Note that the hole-injection layer 71 may be formed to have a single-layer structure using a composite material containing a hole-transport material and an acceptor material (electron-accepting material), or a stacked-layer structure in which a layer containing a hole-transport material and a layer containing an acceptor material (electron-accepting material) are stacked.

The hole-transport layer 72 is a layer transporting the holes, which are injected from the conductive layer 41 by the hole-injection layer 71, into the light-emitting layer 73. Note that the hole-transport layer 72 is a layer containing a hole-transport material. It is particularly preferable that the HOMO level of the hole-transport material used for the hole-transport layer 72 be the same as or close to the HOMO level of the hole-injection layer 71.

Examples of the acceptor material used for the hole-injection layer 71 include oxides of a metal belonging to any of Group 4 to Group 8 of the periodic table. Specific examples include molybdenum oxide, vanadium oxide, niobium oxide, tantalum oxide, chromium oxide, tungsten oxide, manganese oxide, and rhenium oxide. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and the like can be used.

The hole-transport materials used for the hole-injection layer 71 and the hole-transport layer 72 are preferably substances with a hole mobility greater than or equal to 10$^{-6}$ cm$^2$/Vs. Note that other substances can also be used as long as they have a property of transporting more holes than electrons.

Preferred hole-transport materials are π-electron rich heteroaromatic compounds (e.g., carbazole derivatives and indole derivatives) and aromatic amine compounds; specific examples include compounds having an aromatic amine skeleton, such as 4,4'-bis[N-(1-naphthyl)-N-phenyl amino] biphenyl (abbreviation: NPB or α-NPD), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl) phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4"-tris(carbazol-9-yl)triphenylamine (abbreviation: TCTA), 4,4',4"-tris(N,N-diphenylamino)triphenylamine (abbreviation: TDATA), and 4,4',4"-tris[N-(3-methylphenyl)-N-phenyl amino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl] benzene (abbreviation: TCPB), and 9-[4-(10-phenyl-9-anthracenyl)phenyl]-9H-carbazole (abbreviation: CzPA); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl) phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

High molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), and poly[N,N'-bis(4-butylphenyl)-N,N-bis(phenyl)benzidine] (abbreviation: Poly-TPD) can also be used.

Note that the hole-transport material is not limited to the above examples, and one of or a combination of various known materials can be used as the hole-transport material for the hole-injection layer 71 and the hole-transport layer 72. Note that the hole-transport layer 72 may be formed of a plurality of layers. That is, a first hole-transport layer and a second hole-transport layer may be stacked, for example.

<<Light-Emitting Layer 73>>

The light-emitting layer 73 is a layer containing a light-emitting substance. As the light-emitting substance, a substance whose emission color is blue, violet, bluish violet, green, yellowish green, yellow, orange, red, or the like is appropriately used. Here, in the case where the light-emitting element 40 includes a plurality of EL layers as illustrated in FIG. 8C, the EL layers can emit different emission colors by using different light-emitting substances in their respective light-emitting layers 73. Note that a stacked-layer structure in which one light-emitting layer contains different light-emitting substances may be employed.

The light-emitting layer 73 may contain one or more kinds of organic compounds (a host material and an assist material) in addition to a light-emitting substance (a guest material). As the one or more kinds of organic compounds, one or both of the hole-transport material and the electron-transport material can be used.

There is no particular limitation on the light-emitting substance that can be used for the light-emitting layer 73, and it is possible to use a light-emitting substance that converts singlet excitation energy into light in the visible light range or a light-emitting substance that converts triplet excitation energy into light in the visible light range. Examples of the light-emitting substance are given below.

As an example of the light-emitting substance that converts singlet excitation energy into light, a substance that exhibits fluorescence (fluorescent material) can be given; examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N-bis(3-methylphenyl)-N,N-bis[3-(9-phenyl-9H-fluoren-9-yl)phenyl]pyrene-1,6-diamine (abbreviation: 1,6mMemFLPAPm), N,N-diphenyl-N,N-bis[4-(9-phenyl-9H-fluoren-9-yl)phenyl]pyrene-1,6-diamine (abbreviation: 1,6FLPAPm), N,N'-bis(dibenzofuran-2-yl)-N,N-diphenylpyrene-1,6-diamine (abbreviation: 1,6FrAPm), N,N'-bis(dibenzothiophen-2-yl)-N,N-diphenylpyrene-1,6-diamine (abbreviation: 1,6ThAPm), N,N'-(pyrene-1,6-diyl)bis[(N-phenylbenzo[b]naphtho[1,2-d]furan)-6-amine](abbreviation: 1,6BnfAPm), N,N-(pyrene-1,6-diyl)bis[(N-phenylbenzo[b]naphtho[1,2-d]furan)-8-amine](abbreviation: 1,6BnfAPrn-02), and N,N-(pyrene-1,6-diyl)bis[(6,N-diphenylbenzo[b]naphtho[1,2-d]furan)-8-amine] (abbreviation: 1,6BnfAPrn-03). In addition, pyrene derivatives are compounds effective for meeting the chromaticity of blue in one embodiment of the present invention.

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,N',N''-triphenyl-1,4-phenylenedia mine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N''-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit different emission colors (emission peaks), and thus are used through appropriate selection as needed.

As examples of a phosphorescent material that emits blue or green light and whose emission spectrum has a peak wavelength at greater than or equal to 450 nm and less than or equal to 570 nm, the following substances can be given.

Examples include organometallic complexes having a 4H-triazole skeleton, such as tris{2-[5-(2-methylphenyl)-4-(2,6-dimethylphenyl)-4H-1,2,4-triazol-3-yl-$\kappa N^2$]phenyl-$\kappa C$}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-TH-1,2,4-triazolato]iridium(III) (abbreviation: [Ir(Mptzl-mp)$_3$]) and tris(1-methyl-5-phenyl-3-propyl-TH-1,2,4-triazolato)iridium(III) (abbreviation: [Ir(Prptzl-Me)$_3$]); organometallic complexes having an imidazole skeleton, such as fac-tris[1-(2,6-diisopropylphenyl)-2-phenyl-TH-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$] iridium(III) picolinate (abbreviation: FIrpic), bis[2-(3,5-bistrifluoromethyl-phenyl)-pyridinato-N,$C^{2'}$]iridium(III)

picolinate (abbreviation: [Ir(CF$_3$ppy)$_2$(pic)]), and bis[2-(4', 6'-difluorophenyl)pyridinato-N,C$^{2'}$]iridium(III) acetylacetonate (abbreviation: FIr(acac)).

As examples of a phosphorescent material that emits green or yellow light and whose emission spectrum has a peak wavelength at greater than or equal to 495 nm and less than or equal to 590 nm, the following substances can be given.

Examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$ (acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN3]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato) (monophenanthroline)terbium(III) (abbreviation: [Tb(acac)$_3$(Phen)]).

Among the above, organometallic iridium complexes having a pyridine skeleton (particularly, a phenylpyridine skeleton) or a pyrimidine skeleton are compounds effective for meeting the chromaticity of green in one embodiment of the present invention.

As examples of a phosphorescent material that emits yellow or red light and whose emission spectrum has a peak wavelength at greater than or equal to 570 nm and less than or equal to 750 nm, the following substances can be given.

Examples include organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(dlnpm)$_2$(dpm)]); organometallic complexes having a pyrazine skeleton, such as (acetylacetonato) bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O, O')iridium(III) (abbreviation: [Ir(dmdppr-dmCP)$_2$(dpm)]), (acetylacetonato)bis[2-methyl-3-phenylquinoxalinato-N, C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]).

Among the above, organometallic iridium complexes having a pyrazine skeleton are compounds effective for meeting the chromaticity of red in one embodiment of the present invention. In particular, organometallic iridium complexes having a cyano group, such as [Ir(dmdppr-dmCP)$_2$(dpm)], are preferable because of their high stability.

Note that as the blue-light-emitting substance, a substance whose photoluminescence peak wavelength is greater than or equal to 430 nm and less than or equal to 470 nm, preferably greater than or equal to 430 nm and less than or equal to 460 nm is used. As the green-light-emitting substance, a substance whose photoluminescence peak wavelength is greater than or equal to 500 nm and less than or equal to 540 nm, preferably greater than or equal to 500 nm and less than or equal to 530 nm is used. As the red-light-emitting substance, a substance whose photoluminescence peak wavelength is greater than or equal to 610 nm and less than or equal to 680 nm, preferably greater than or equal to 620 nm and less than or equal to 680 nm is used. Note that the photoluminescence may be measured with either a solution or a thin film.

With the parallel use of such compounds and the microcavity effect, the above chromaticity can be met more easily. Here, a semi-transmissive and semi-reflective electrode (a metal thin film portion) that is needed for obtaining microcavity effect preferably has a thickness of greater than or equal to 20 nm and less than or equal to 40 nm. Further preferably, the thickness is greater than 25 nm and less than or equal to 40 nm. However, the thickness greater than 40 nm possibly reduces the efficiency.

As the organic compounds (the host material and the assist material) used in the light-emitting layer 73, one or more kinds of substances having an energy gap larger than the energy gap of the light-emitting substance (the guest material) are used. Note that the hole-transport materials listed above and the electron-transport materials given below can be used as the host material and the assist material, respectively.

In the case where the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specific examples include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) higher than that of the light-emitting substance can be selected as the host material. In this case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, or the like.

Specific examples include metal complexes such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)-tris(1-phenyl-1H-benzimidazole) (abbreviation: TPBI), bathophenanthroline (abbreviation: BPhen), bathocuproine (abbreviation: BCP), 2,9-bis(naphthalen-2-yl)-4,7-diphenyl-1,10-phenanthroline (abbreviation: NBphen), and 9-[4-(5-phenyl-1,3,4-oxadiazol-2-yl)phenyl]-9H-carbazole (abbreviation: CO11); and aromatic amine compounds such as NPB, TPD, and BSPB.

In addition, condensed polycyclic aromatic compounds such as anthracene derivatives, phenanthrene derivatives, pyrene derivatives, chrysene derivatives, and dibenzo[g,p]chrysene derivatives can be used; specifically, it is possible to use, for example, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 9,10-diphenyl-2-[N-phenyl-N-(9-phenyl-9H-carbazol-3-yl)amino]anthracene (abbreviation: 2PCAPA), 6,12-dimethoxy-5,11-diphenylchrysene, N,N,N',N',N",N",N"',N"'-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl) diphenanthrene (abbreviation: DPNS2), or 1,3,5-tri(1-pyrenyl)benzene (abbreviation: TPB3).

In the case where a plurality of organic compounds are used for the light-emitting layer 73, compounds that form an exciplex are preferably used in combination with a light-emitting substance. In this case, various organic compounds can be used in appropriate combination; to form an exciplex efficiently, it is particularly preferable to combine a compound that easily accepts holes (hole-transport material) and a compound that easily accepts electrons (electron-transport material). As the hole-transport material and the electron-transport material, specifically, any of the materials described in this embodiment can be used.

The TADF material is a material that can up-convert a triplet excited state into a singlet excited state (reverse intersystem crossing) using a little thermal energy and efficiently exhibits light emission (fluorescence) from the singlet excited state. The thermally activated delayed fluorescence is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV Note that delayed fluorescence by the TADF material refers to light emission having the same spectrum as normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP).

Alternatively, it is possible to use a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (PIC-TRZ), 2-{4-[3-(N-phenyl-9H-carbazol-3-yl)-9H-carbazol-9-yl]phenyl}-4,6-diphenyl-1,3,5-triazine (PCCzPTzn), 2-[4-(10H-phenoxazin-10-yl)phenyl]-4,6-diphenyl-1,3,5-triazine (PXZ-TRZ), 3-[4-(5-phenyl-5,10-dihydrophenazin-10-yl)phenyl]-4,5-diphenyl-1,2,4-triazole (PPZ-3TPT), 3-(9,9-dimethyl-9H-acridin-10-yl)-9H-xanthen-9-one (ACRXTN), bis[4-(9,9-dimethyl-9,10-dihydroacridine)phenyl]sulfone (DMAC-DPS), or 10-phenyl-10H,10'H-spiro[acridin-9,9'-anthracen]-10'-one (ACRSA). Note that a substance in which a π-electron rich heteroaromatic ring is directly bonded to a π-electron deficient heteroaromatic ring is particularly preferable because both the donor property of the π-electron rich heteroaromatic ring and the acceptor property of the π-electron deficient heteroaromatic ring are improved and the energy difference between the singlet excited state and the triplet excited state becomes small.

Note that the TADF material can also be used in combination with another organic compound.

<<Electron-Transport Layer 74>>

The electron-transport layer 74 is a layer transporting the electrons, which are injected from the conductive layer 43 by the electron-injection layer 75, to the light-emitting layer 73. Note that the electron-transport layer 74 is layer containing an electron-transport material. The electron-transport material used for the electron-transport layer 74 is preferably a substance with an electron mobility of higher than or equal to $1\times10^{-6}$ cm$^2$/Vs. Note that any other substance can also be used as long as the substance transports more electrons than holes.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use any of metal complexes such as Alq$_3$, tris(4-methyl-8-quinolinolato)aluminum(III) (abbreviation: Almq$_3$), bis(10-hydroxybenzo[h]quinolinato) beryllium(II) (abbreviation: BeBq$_2$), BAlq, Zn(BOX)$_2$, and bis[2-(2-hydroxyphenyl)benzothiazolato]zinc(II) (abbreviation: Zn(BTZ)$_2$); heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOS); and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Furthermore, a high-molecular compound such as poly (2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

The electron-transport layer 74 is not limited to a single layer and may be a stack of two or more layers each containing any of the above substances.

<<Electron-Injection Layer 75>>

The electron-injection layer 75 is a layer containing a substance having a high electron-injection property. The electron-injection layer 75 can be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound like erbium fluoride (ErF$_3$) can also be used. An electride may also be used for the electron-injection layer 75. Examples of the electride include a substance in which electrons are added at high concentration to a mixed oxide of calcium and aluminum. Any of the above-described substances used for the electron-transport layer 74 can also be used.

A composite material in which an organic compound and an electron donor (donor) are mixed may also be used for the electron-injection layer 75. Such a composite material is excellent in an electron-injection property and an electron-transport property because electrons are generated in the organic compound by the electron donor. The organic compound here is preferably a material excellent in transporting the generated electrons; specifically, for example, the electron-transport material used for the electron-transport layer 74 (e.g., a metal complex or a heteroaromatic compound) can be used. As the electron donor, a substance showing an electron-donating property with respect to an organic compound is used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. Alternatively, a Lewis base such as magnesium oxide can be used. Further alternatively, an organic compound such as tetrathiafulvalene (abbreviation: TTF) can be used.

<<Charge-Generation Layer 44>>

The charge generation layer 44 (the charge generation layer 44a and the charge generation layer 44b) has a function of injecting electrons into the EL layer 42 on a side closer to the conductive layer 41, of the two EL layers 42 in contact with the charge generation layer 44, and injecting holes into the EL layer 42 on a side closer to the conductive layer 43, when a voltage is applied between the conductive layer 41 and the conductive layer 43. Note that the charge generation layer 44 may have either a structure in which an electron acceptor (acceptor) is added to a hole-transport material or a structure in which an electron donor (donor) is added to an electron-transport material. Alternatively, both of these structures may be stacked. Note that forming the charge generation layer 44 with the use of any of the above materials can suppress an increase in drive voltage of the semiconductor device of one embodiment of the present invention in the case where the EL layers are stacked.

When the charge generation layer 44 has a structure in which an electron acceptor is added to a hole-transport material, the electron acceptor can be 7,7,8,8-tetracyano-2,3,5,6-tetrafluoroquinodimethane (abbreviation: F$_4$-TCNQ), chloranil, or the like. Other examples include oxides of metals that belong to Group 4 to Group 8 of the periodic table. Specific examples are vanadium oxide, niobium oxide, tantalum oxide, chromium oxide, molybdenum oxide, tungsten oxide, manganese oxide, and rhenium oxide.

When the charge generation layer 44 has a structure in which an electron donor is added to an electron-transport material, an alkali metal, an alkaline earth metal, a rare earth metal, or a metal that belongs to Group 2 or Group 13 of the periodic table, or an oxide or carbonate thereof can be used as the electron donor. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

For fabrication of the light-emitting element 40, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layer, the hole-transport layer, the light-emitting layer, the electron-transport layer, and the electron-injection layer) included in the EL layer and the charge generation layer of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, a screen printing (stencil) method, an offset printing (planography) method, a flexography (relief printing) method, a gravure printing method, or a micro-contact printing method), or the like.

Note that materials for the functional layers (the hole-injection layer, the hole-transport layer, the light-emitting layer, the electron-transport layer, and the electron-injection layer) included in the EL layer and the charge generation layer of the light-emitting element described in this embodiment are not limited to the above materials, and other materials can be used in combination as long as the functions of the layers are fulfilled. For example, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. As the quantum dot material, a colloidal quantum dot material, an alloyed quantum dot material, a core-shell quantum dot material, a core quantum dot material, or the like can be used.

<Cross-Sectional Structure Example 2 of Pixel>

Figure 9:
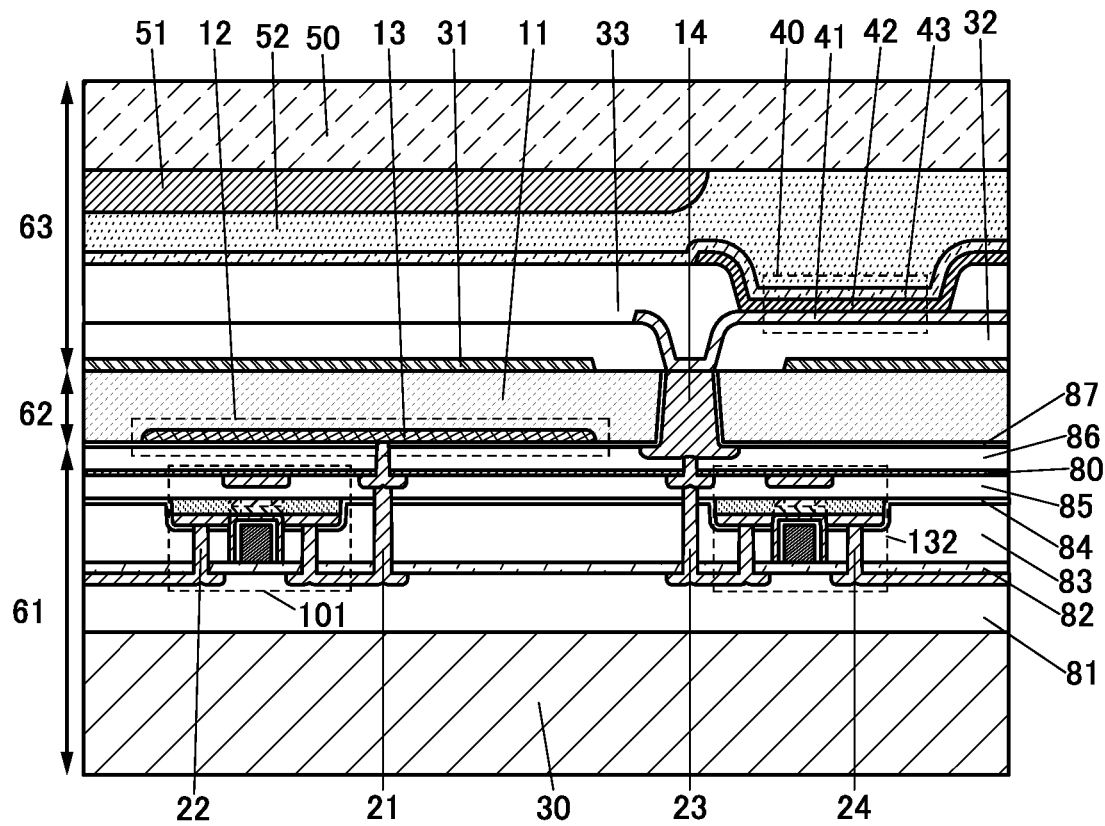
FIG. 9 is a diagram illustrating a structure example of a semiconductor device.

FIG. 9 is a cross-sectional view illustrating a structure example of the pixel 10, and is a modification example of the pixel 10 having the structure illustrated in FIG. 3. The pixel 10 having the structure illustrated in FIG. 9 is different from the pixel 10 having the structure illustrated in FIG. 3 in that the EL layer 42 is formed by separate coloring.

In the case of the pixel 10 having the structure illustrated in FIG. 3, the EL layer 42 emitting white light and infrared light is provided in each pixel 10, for example. In contrast, in the case of the pixel 10 having the structure illustrated in FIG. 9, the EL layer 42 emitting red light, the EL layer 42 emitting green light, the EL layer 42 emitting blue light, and the EL layer 42 emitting infrared light are formed by separate coloring, for example. Therefore, the filter 51 is not necessarily provided to include a region overlapping with the light-emitting element 40. Accordingly, light emitted from the light-emitting element 40 can be inhibited from being absorbed by the filter 51. Thus, the semiconductor device of one embodiment of the present invention can emit high-luminance light and the semiconductor device of one embodiment of the present invention can have reduced power consumption. Note that also in the pixel 10 having the structure illustrated in FIG. 9, the filter 51 may be provided to include a region overlapping with the light-emitting element 40. In this case, the semiconductor device of one embodiment of the present invention can emit light with higher color purity.

Figure 10A:
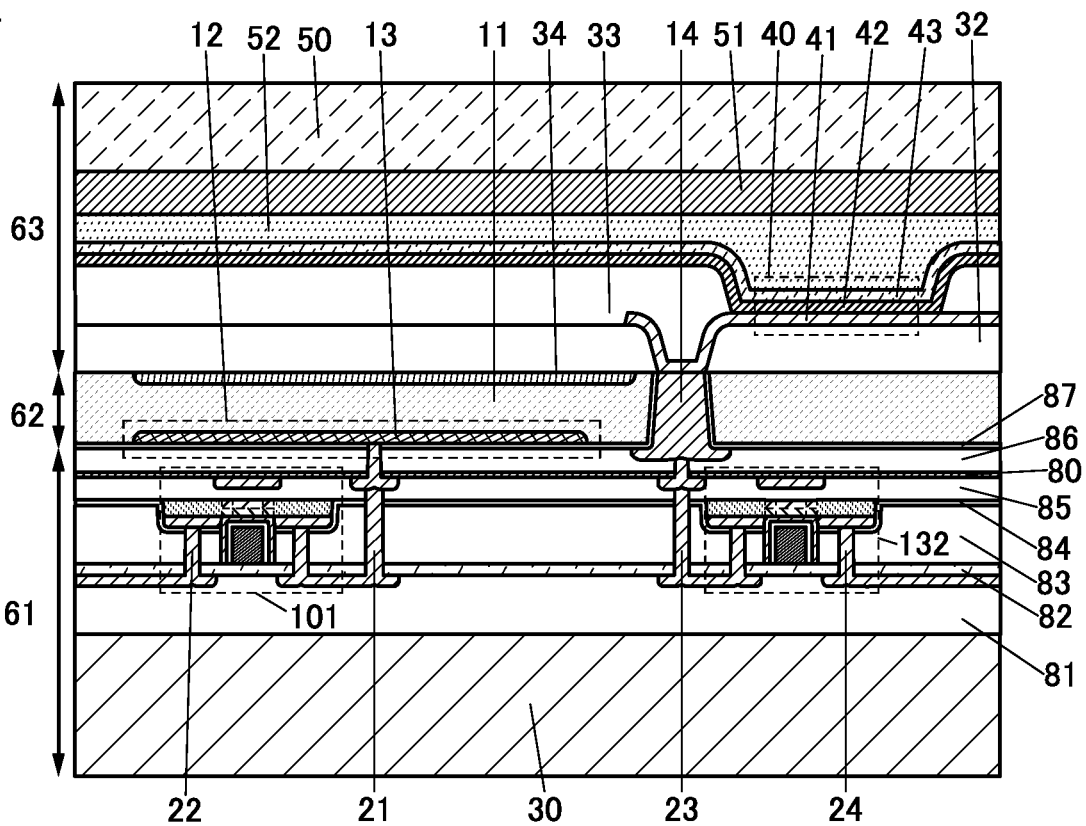
FIG. 10A and FIG. 10B are diagrams each illustrating a structure example of a semiconductor device.

FIG. 10A is a cross-sectional view illustrating a structure example of the pixel 10, and is a modification example of the pixel 10 having the structure illustrated in FIG. 3. The pixel 10 having the structure illustrated in FIG. 10A is different from the pixel 10 having the structure illustrated in FIG. 3 in that the conductive layer 31 is not formed over the back surface of the substrate 11 and a low-resistance region 34 is formed on the back surface side of the substrate 11.

The low-resistance region 34 can be formed in such a manner that the back surface of the substrate 11 is polished as illustrated in FIG. 6A and then impurities are added to the back surface of the substrate 11. For example, adding a trivalent element can make the low-resistance region 34 a p-type region, and adding a pentavalent element can make the low-resistance region 34 an n-type region. Note that the low-resistance region 34 can be a p-type region in the case where the substrate 11 is a p-type substrate, and the low-resistance region 34 can be an n-type region in the case where the substrate 11 is an n-type substrate. Examples of the method for adding the above impurities include an ion implantation method, an ion doping method, and a plasma immersion ion implantation method.

Figure 10B:
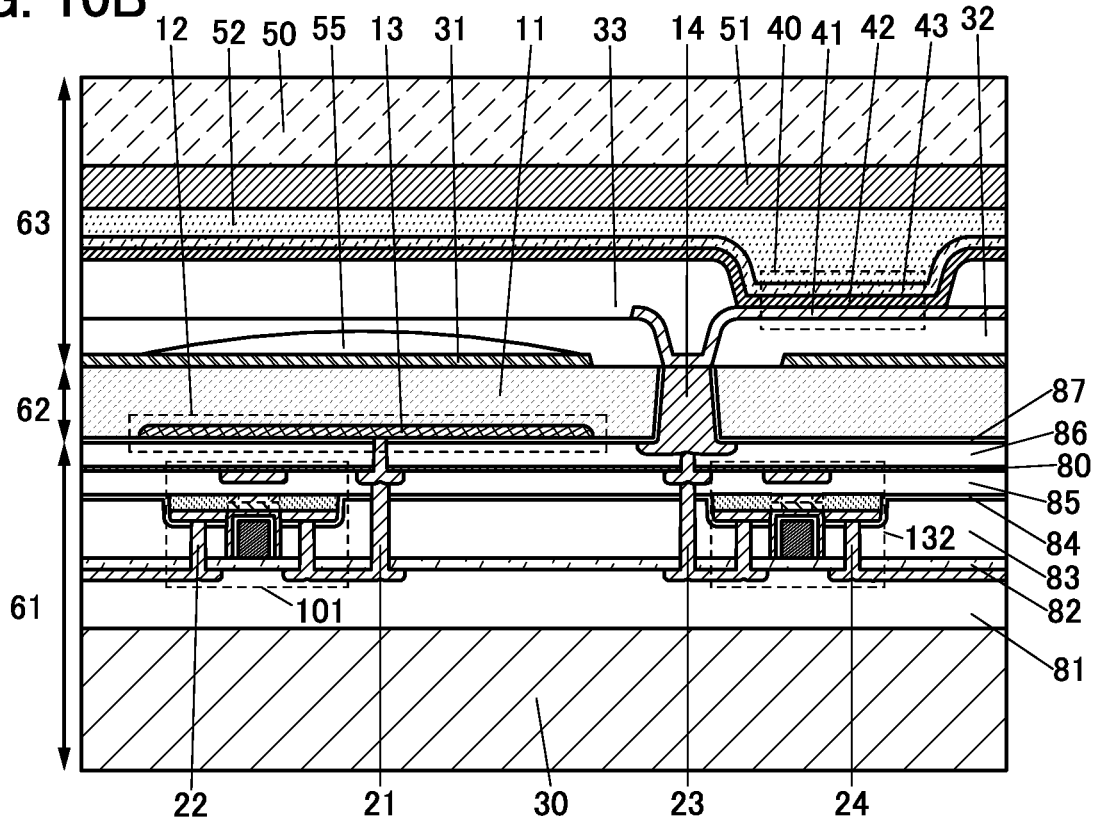

FIG. 10B is a cross-sectional view illustrating a structure example of the pixel 10, and is a modification example of the pixel 10 having the structure illustrated in FIG. 3. The pixel 10 having the structure illustrated in FIG. 10B is different from the pixel 10 having the structure illustrated in FIG. 3 in that a microlens 55 is provided in the layer 63.

The microlens 55 is provided to include a region overlapping with the photoelectric conversion element 12. Accordingly, light is incident on the photoelectric conversion element 12 in a vertical direction, so that the photoelectric conversion element 12 can have higher light detection sensitivity.

Although the microlens 55 is provided to be covered with the insulating layer 32 in FIG. 10B, one embodiment of the present invention is not limited thereto. For example, the microlens 55 may be provided to be covered with the insulating layer 33. Alternatively, a microlens array may be provided both in the layer 63 and over the layer 63 (see FIG. 4).

<Cross-Sectional Structure Example 3 of Pixel>

FIG. 11 is a cross-sectional view illustrating a structure example of the pixel 10. In the pixel 10 having the structure illustrated in FIG. 11, the transistor 101, the transistor 132, the photoelectric conversion element 12, the light-emitting element 40, and the like are provided between a substrate 60 and the substrate 50.

The pixel 10 having the structure illustrated in FIG. 11 can have a stacked-layer structure of the layer 61 and a layer 64. In the layer 61, the substrate 60, the insulating layer 86, the insulating layer 80, the transistor 101, the transistor 132, and the insulating layer 82 are provided. The transistor 101 and the transistor 132 are provided between the insulating layer 80 and the insulating layer 82. The insulating layer 85 and the insulating layer 84 are provided to cover the channel formation regions, the source regions, and the drain regions of the transistor 101 and the transistor 132. In addition, the insulating layer 83 is provided between the insulating layer 84 and the insulating layer 82.

The conductive layer 21 is provided to be electrically connected to one of the source and the drain of the transistor 101, and the conductive layer 22 is provided to be electrically connected to the other of the source and the drain of the transistor 101. The conductive layer 23 is provided to be electrically connected to one of the source and the drain of the transistor 132, and the conductive layer 24 is provided to be electrically connected to the other of the source and the drain of the transistor 132.

As the substrate 60, a silicon substrate, a glass substrate, a ceramics substrate, a resin substrate, or the like can be used. Note that a transistor or the like can be provided between the substrate 60 and the transistors 101 and 132. For example, in the case where a silicon substrate is used as the substrate 60, a Si transistor can be provided.

In the layer 64, the insulating layer 32, the light-emitting element 40, the photoelectric conversion element 12, and the insulating layer 33 are provided. The substrate 50 and the filter 51 are also provided in the layer 64. The substrate 50 and the substrate 60 are sealed with the sealing layer 52.

The insulating layer 32 is provided to cover the conductive layer 21 to the conductive layer 24, and the light-emitting element 40 and the photoelectric conversion element 12 are provided over the insulating layer 32.

The light-emitting element 40 has a stacked-layer structure in which the conductive layer 41, the EL layer 42, and the conductive layer 43 are stacked in this order from the insulating layer 32 side. The photoelectric conversion element 12 has a structure in which a conductive layer 45, an active layer 46, and the conductive layer 43 are stacked in this order from the insulating layer 32 side.

Here, the conductive layer 41 and the conductive layer 45 can be formed through the same process. Specifically, an insulating film is formed over the conductive layer 21 to the conductive layer 24 and the insulating layer 82, and an opening portion reaching the conductive layer 21 and an opening portion reaching the conductive layer 23 are provided in the insulating film, whereby the insulating layer 32 is formed. Next, a conductive film is formed over the insulating layer 32 and in the opening portion, and then patterning is performed by a photolithography method or the like. Then, the conductive film is processed along the formed pattern by an etching method or the like. In the above manner, the conductive layer 41 and the conductive layer 45 can be formed.

The conductive layer 43 can serve as both the common electrode of the light-emitting element 40 and the common electrode of the photoelectric conversion element 12. Thus, when the pixel 10 has the structure illustrated in FIG. 11, the fabrication process of the semiconductor device of one embodiment of the present invention can be simplified. Therefore, the semiconductor device of one embodiment of the present invention can be inexpensive.

The conductive layer 41 is electrically connected to the conductive layer 23 through the opening provided in the insulating layer 32. The conductive layer 45 is electrically connected to the conductive layer 21 through the opening provided in the insulating layer 32. The insulating layer 33 is provided to cover an end of the conductive layer 41 and an end of the conductive layer 45.

For the conductive layer 41 and the conductive layer 45, a low-resistance conductive film of a metal or the like can be used. For example, the conductive layer 41 and the conductive layer 45 can be formed using one or more kinds of metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

The conductive layer 45 has a function of an electrode of the photoelectric conversion element 12. Thus, it can be said that one electrode of the photoelectric conversion element 12 is electrically connected to one of the source and the drain of the transistor 101 through the conductive layer 21.

The active layer 46 can have a stacked-layer structure in which a p-type semiconductor and an n-type semiconductor are stacked to form a pn junction; or a stacked-layer structure in which a p-type semiconductor, an i-type semiconductor, and an n-type semiconductor are stacked to form a pin junction, for example.

As the semiconductor used for the active layer 46, an inorganic semiconductor such as silicon or an organic semiconductor containing an organic compound can be used. It is particularly preferable to use an organic semiconductor material because the EL layer 42 of the light-emitting element 40 and the active layer 46 can be formed with the same manufacturing apparatus.

In the case where an organic semiconductor material is used for the active layer 46, an electron-accepting organic semiconductor material such as fullerene (e.g., $C_{60}$ or $C_{70}$) or its derivative can be used as an n-type semiconductor material. As a p-type semiconductor material, an electron-donating organic semiconductor material such as copper(II) phthalocyanine (abbreviation: CuPc) or 5,10,15,20-tetraphenylbisbenzo[5,6]indeno[1,2,3-cd:1',2',3'-lm]perylene (abbreviation: DBP) can be used. The active layer 46 may have a stacked-layer structure (a p-n stacked-layer structure) including an electron-accepting semiconductor material and an electron-donating semiconductor material, or a stacked-layer structure (a p-i-n stacked-layer structure) in which a bulk heterostructure layer formed by co-evaporation of an electron-accepting semiconductor material and an electron-donating semiconductor material is provided therebetween. Furthermore, a layer functioning as a hole-blocking layer or a layer functioning as an electron-blocking layer may be provided around (above or below) the p-n stacked-layer structure or the p-i-n stacked-layer structure, in order to inhibit dark current caused when light is not applied.

In the case where the pixel 10 has the structure illustrated in FIG. 11, it is unnecessary to provide the substrate 11 in the pixel 10. Thus, when a substrate having flexibility (hereinafter also referred to as a flexible substrate) is used as the substrate 60 and the substrate 50, for example, the semiconductor device of one embodiment of the present invention can be a semiconductor device having flexibility.

The flexible substrate is preferably a substrate using a film, particularly preferably a substrate using a resin film. In this case, the semiconductor device of one embodiment of the present invention can have higher flexibility and can be reduced in weight and thickness.

For the flexible substrate, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyether sulfone (PES) resin, a polyamide resin (e.g., nylon or aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, or cellulose nanofiber can be used, for example. Alternatively, glass that is thin enough to have flexibility may be used.

<Circuit Configuration Example of Pixel>

FIG. 12 is a circuit diagram illustrating a configuration example of the pixel 10. The pixel 10 includes the imaging circuit 100 provided with the photoelectric conversion element 12 and a display circuit 130 provided with the light-emitting element 40.

<<Circuit Configuration Example of Imaging Circuit>>

The imaging circuit 100 includes the transistor 101, a transistor 102, a transistor 103, a transistor 104, and a capacitor 105 in addition to the photoelectric conversion element 12. Note that a configuration in which the capacitor 105 is not provided may be employed.

One electrode of the photoelectric conversion element 12 is electrically connected to one of the source and the drain of the transistor 101. The one of the source and the drain of the transistor 101 is electrically connected to one of a source and a drain of the transistor 102. The one of the source and the drain of the transistor 102 is electrically connected to a gate of the transistor 103. The gate of the transistor 103 is electrically connected to one electrode of the capacitor 105. One of a source and a drain of the transistor 103 is electrically connected to one of a source and a drain of the transistor 104.

A node where the one of the source and the drain of the transistor 101, the one of the source and the drain of the transistor 102, the gate of the transistor 103, and the one electrode of the capacitor 105 are connected is a node FD. The node FD can function as a charge accumulation portion.

A gate of the transistor 101 is electrically connected to a wiring 111. A gate of the transistor 102 is electrically connected to a wiring 112. A gate of the transistor 104 is electrically connected to a wiring 114. The other electrode of the photoelectric conversion element 12 is electrically connected to a wiring 121. The other of the source and the drain of the transistor 102 is electrically connected to a wiring 122. The other of the source and the drain of the transistor 104 is electrically connected to a wiring 124. The other electrode of the capacitor 105 is electrically connected to a wiring 125.

The wiring 111, the wiring 112, and the wiring 114 each have a function of a scan line, and the conduction of the transistors can be controlled with signals supplied to the gates of the transistors through the wiring 111, the wiring 112, and the wiring 114. The wiring 124 has a function of a data line, and imaging data obtained by the photoelectric conversion element 12 is output to the outside of the imaging circuit 100 through the wiring 124.

The wiring 121, the wiring 122, and the wiring 125 each have a function of a power supply line. The imaging circuit 100 illustrated in FIG. 12 has a configuration in which the cathode of the photoelectric conversion element 12 is electrically connected to one of the source and the drain of the transistor 101 and the anode of the photoelectric conversion element 12 is electrically connected to the wiring 121. Thus, the node FD can be reset to a high potential in the operation with the wiring 121 being set to a low potential and the wiring 122 being set to a high potential, so that the photoelectric conversion element 12 can be operated with a reverse bias. Note that the wiring 125 can be set to a low potential.

In this specification and the like, a high potential refers to a potential higher than a low potential. For example, the high potential can be a positive potential and the low potential can be a ground potential or a negative potential.

The transistor 101 has a function of a transfer transistor. When the transistor 101 is brought into a conduction state, the potential of the node FD can be set to a potential corresponding to the amount of light exposure to the photoelectric conversion element 12. Thus, the imaging circuit 100 can obtain imaging data.

The transistor 102 has a function of a reset transistor. When the transistor 102 is brought into a conduction state, the potential of the node FD can be reset to the potential of the wiring 122.

The transistor 103 has a function of an amplifier transistor and can perform output in accordance with the potential of the node FD.

The transistor 104 has a function of a selection transistor. When the transistor 104 is brought into a conduction state, imaging data can be output to the wiring 124. Specifically, the current of the wiring 124 can have a value corresponding to the imaging data.

<<Configuration Example of Display Circuit>>

The display circuit 130 includes a transistor 131, the transistor 132, a transistor 133, and a capacitor 134 in addition to the light-emitting element 40.

One of a source and a drain of the transistor 131 is electrically connected to a gate of the transistor 132. The gate of the transistor 132 is electrically connected to one electrode of the capacitor 134. One of a source and a drain of the transistor 132 is electrically connected to one of a source and a drain of the transistor 133. The one of the source and the drain of the transistor 133 is electrically connected to the other electrode of the capacitor 134. The other electrode of the capacitor 134 is electrically connected to one electrode of the light-emitting element 40.

The other of the source and the drain of the transistor 131 is electrically connected to a wiring 141. The other of the source and the drain of the transistor 132 is electrically connected to a wiring 142. The other of the source and the drain of the transistor 133 is electrically connected to a wiring 143. A gate of the transistor 131 and a gate of the transistor 133 are electrically connected to a wiring 144. The other electrode of the light-emitting element 40 is electrically connected to a wiring 145.

The wiring 141 has a function of a data line, and data including information on the emission luminance of the light-emitting element 40 is supplied to the display circuit 130 through the wiring 141. The wiring 143 has a function of a monitor line, and the electrical characteristics or the like of the light-emitting element 40 can be detected by detection of current flowing through the wiring 143, for example. The wiring 144 has a function of a scan line, and the conduction of the transistor 131 and the transistor 133 can be controlled with signals supplied to the gates of the transistor 131 and the transistor 133 through the wiring 144.

The wiring 142 and the wiring 145 each have a function of a power supply line. The display circuit 130 illustrated in FIG. 12 has a configuration in which the anode of the light-emitting element 40 is electrically connected to one of the source and the drain of the transistor 132 and the cathode of the light-emitting element 40 is electrically connected to the wiring 145. Thus, the light-emitting element 40 can be operated with a forward bias with the wiring 142 being set to a high potential and the wiring 145 being set to a low potential, so that current whose amount corresponds to data supplied to the display circuit 130 can flow into the light-emitting element 40. Thus, the light-emitting element 40 can emit light with a luminance corresponding to the data supplied to the display circuit 130.

When the transistor 131 is brought into a conduction state in the display circuit 130 having the configuration illustrated in FIG. 12, the gate potential of the transistor 132 can be a potential corresponding to data supplied through the wiring 141. Thus, the data can be written to the display circuit 130.

The transistor 132 has a function of a driving transistor, and current flowing into the light-emitting element 40 can be controlled in accordance with a potential supplied to the transistor.

When the transistor 133 is brought into a conduction state, current can flow through the wiring 143. Thus, the electrical characteristics or the like of the light-emitting element 40 can be obtained.

FIG. 12 illustrates a configuration in which the imaging circuit 100 and the display circuit 130 are not electrically connected to each other. In this case, the imaging circuit 100 and the display circuit 130 can be controlled independently. Note that in the case where the imaging circuit 100 and the display circuit 130 are electrically connected to each other, the operation of the imaging circuit 100 and the operation of the display circuit 130 can be controlled dependently on each other.

<Configuration Example of Semiconductor Device>

FIG. 13A is a block diagram illustrating a configuration example of a semiconductor device of one embodiment of the present invention. The semiconductor device includes the pixel array 151 including the pixels 10 arranged in a matrix, a gate driver circuit 152, and a source driver circuit 153. The imaging circuit 100 and the display circuit 130 are provided in the pixel 10.

The gate driver circuit 152 has a function of selecting a row of the pixel array 151. The source driver circuit 153 has a function of generating data that is to be supplied to the display circuit 130. In addition, the source driver circuit 153 has a function of receiving imaging data obtained by the imaging circuit 100 and outputting the imaging data to the outside of the semiconductor device.

Figure 13B:
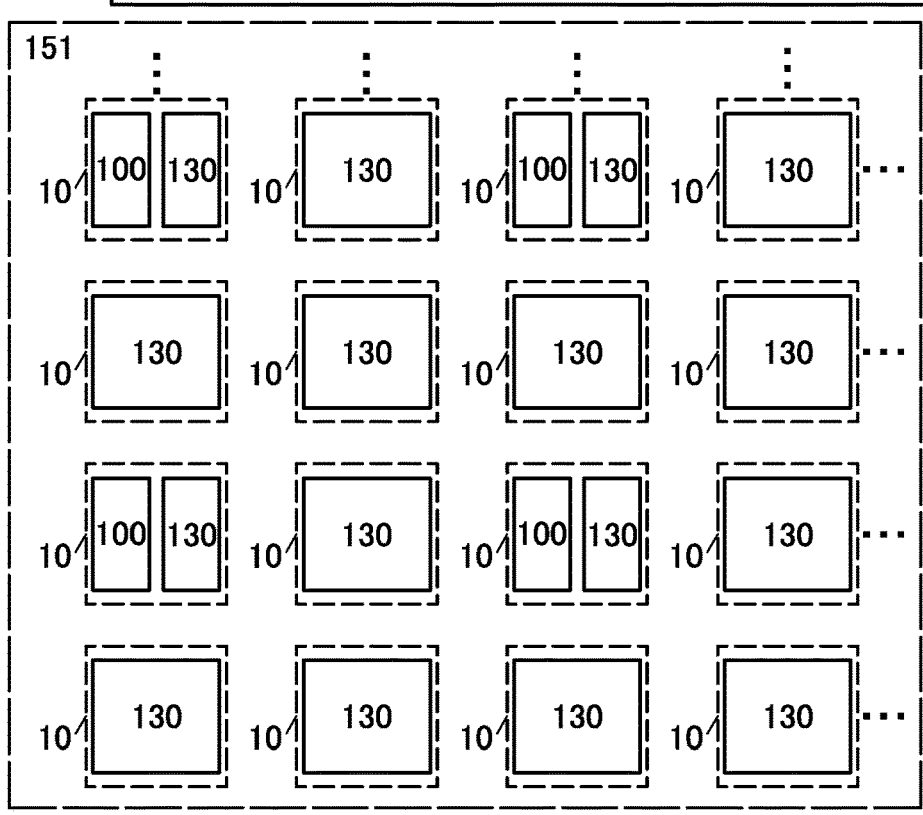

Although all the pixels 10 include both the imaging circuit 100 and the display circuit 130 in the semiconductor device illustrated in FIG. 13A, one embodiment of the present invention is not limited thereto. FIG. 13B is a diagram illustrating a configuration example of the pixel array 151, and is a modification example of the pixel array 151 having the configuration illustrated in FIG. 13A. The pixel array 151 having the configuration illustrated in FIG. 13B is different from the pixel array 151 having the configuration illustrated in FIG. 13A in that the imaging circuits 100 are provided only in some of the pixels 10.

In the semiconductor device including the pixel array 151 having the configuration illustrated in FIG. 13B, the opening area of the display circuit 130 can be increased. Thus, the semiconductor device of one embodiment of the present invention can emit high-luminance light and the semiconductor device of one embodiment of the present invention can have reduced power consumption.

As the transistor 101 and the transistor 102 included in the imaging circuit 100 illustrated in FIG. 12 and the like, OS transistors are preferably used. The OS transistor has a feature of an extremely low off-state current. When OS transistors are used as the transistor 101 and the transistor 102, a period during which charge can be retained at the node FD can be elongated greatly. Therefore, a global shutter system in which a charge accumulation operation is performed in all the pixels at the same time can be used without complicating the circuit configuration and operation method.

FIG. 14A is a schematic view of an operation method with a rolling shutter system, and FIG. 14B is a schematic view of a global shutter system. Note that En denotes exposure (accumulation operation) in an n-th column (n is a natural number), and Rn denotes reading operation in the n-th column. FIG. 14A and FIG. 14B each show an operation from a first row (Line[1]) to an M-th row (Line[M]) (M is a natural number).

The rolling shutter system is an operation method in which the light exposure and data reading are performed sequentially and a reading period of a row overlaps with a light exposure period of another row. The reading operation is performed immediately after the light exposure, so that imaging can be performed even with a circuit configuration having a relatively short data retention period. However, one frame image is formed with imaging data obtained not simultaneously, resulting in a distorted image in the case of imaging a moving object.

In contrast, the global shutter system is an operation method in which light exposure is performed on all the pixels simultaneously, data is retained in each pixel, and data reading is performed row by row. Thus, an image without distortion can be obtained even in the case of imaging a moving object.

In the case where a transistor with a relatively high off-state current, such as a Si transistor, is used in a pixel, a rolling shutter system is used because charges easily leak from a charge accumulation portion. In order to achieve a global shutter system using a Si transistor, it is necessary to separately provide a memory circuit or the like and to perform more complicated operation at high speed. In contrast, in the case where an OS transistor is used in a pixel, there is little charge leakage from the charge accumulation portion, so that the global shutter system can be easily achieved.

Note that OS transistors may be used also as the transistor 103 and the transistor 104. Furthermore, OS transistors may be used also as the transistor 131 to the transistor 133 included in the display circuit 130. When one kind of transistor such as OS transistor is used as all the transistors included in the semiconductor device of one embodiment of the present invention, the fabrication process of the semiconductor device of one embodiment of the present invention can be simplified. Therefore, the semiconductor device of one embodiment of the present invention can be inexpensive. Note that all or some of the transistor 101 to the transistor 104 and the transistor 131 to the transistor 133 may be Si transistors. Examples of the Si transistor include a transistor containing amorphous silicon and a transistor containing crystalline silicon (typically, low-temperature polysilicon, single crystal silicon, or the like).

Figure 15:
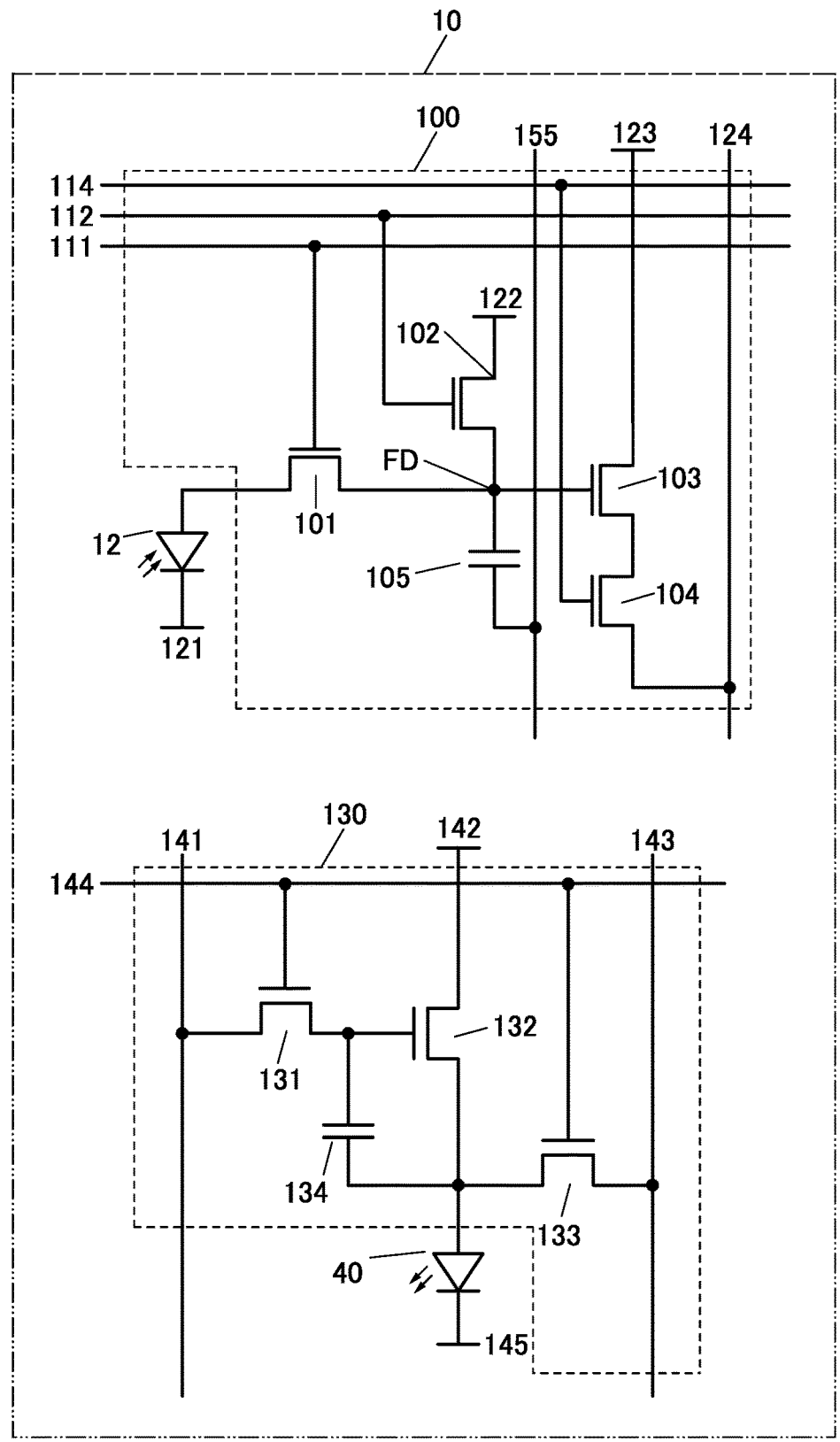
FIG. 15 is a diagram illustrating a configuration example of a pixel.

FIG. 15 is a circuit diagram illustrating a configuration example of the pixel 10, and is a modification example of the pixel 10 having the configuration illustrated in FIG. 12. The pixel 10 having the configuration illustrated in FIG. 15 is different from the pixel 10 having the configuration illustrated in FIG. 12 in that the other electrode of the capacitor 105 included in the imaging circuit 100 is electrically connected to the wiring 155 having a function of a data line, not to the wiring 125 having a function of a power supply line.

In the imaging circuit 100 having the configuration illustrated in FIG. 15, data can be supplied to the other electrode of the capacitor 105 through the wiring 155. The data can be added to imaging data obtained using the photoelectric conversion element 12. Thus, imaging data obtained by the imaging circuit 100 can be corrected, for example. The imaging data obtained by the imaging circuit 100 can be subjected to imaging processing such as noise removal, for example.

Note that the imaging circuit 100 illustrated in FIG. 15 has a configuration in which the anode of the photoelectric conversion element 12 is electrically connected to one of the source and the drain of the transistor 101, and the cathode of the photoelectric conversion element 12 is electrically connected to the wiring 121. Thus, the node FD can be reset to a low potential in the operation with the wiring 121 being set to a high potential and the wiring 122 being set to a low potential, so that the photoelectric conversion element 12 can be operated with a reverse bias.

Figure 16:
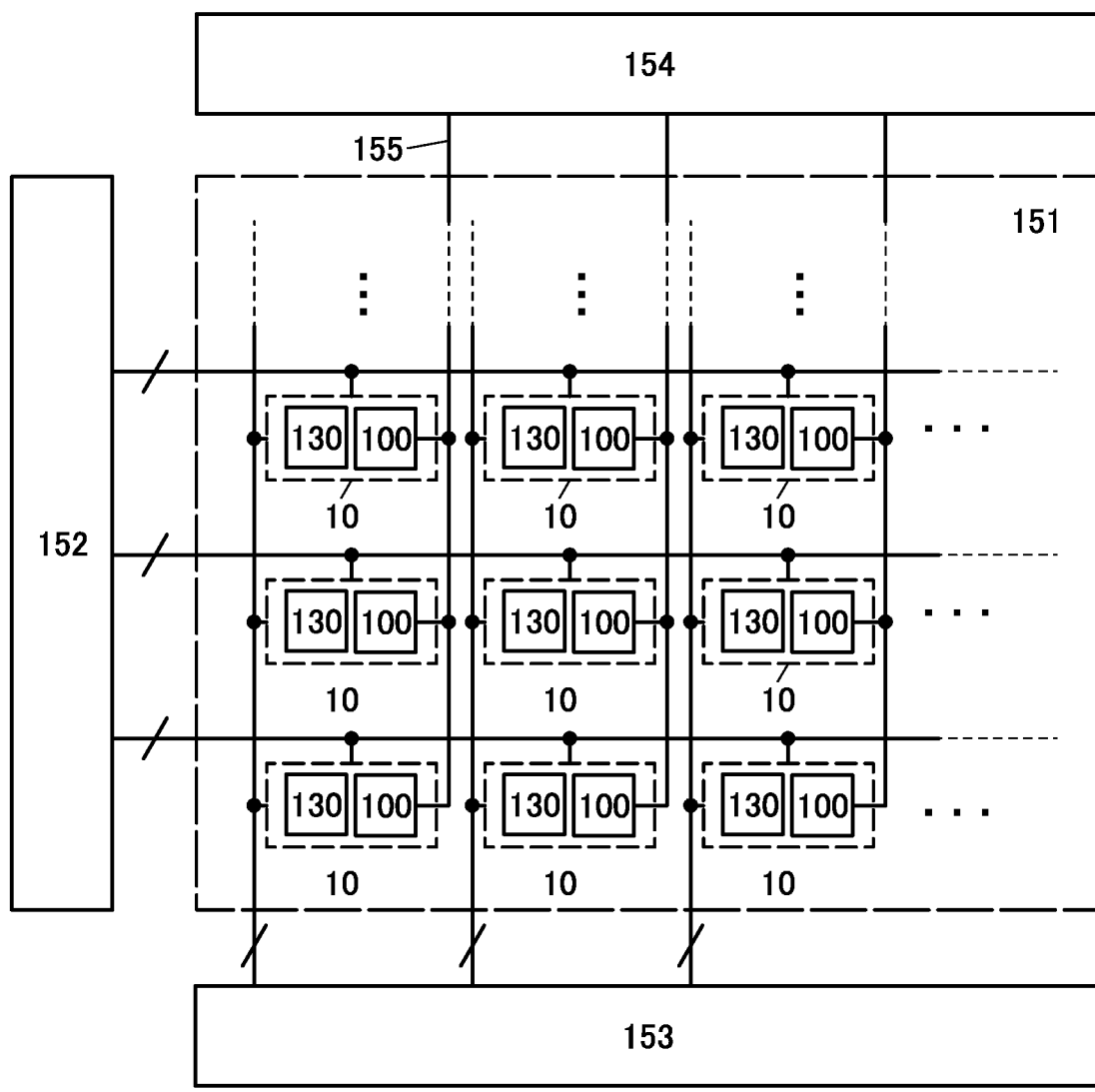
FIG. 16 is a diagram illustrating a configuration example of a semiconductor device.

FIG. 16 is a block diagram illustrating a configuration example of the semiconductor device of one embodiment of the present invention, and is a modification example of the semiconductor device having the configuration illustrated in FIG. 13A. The semiconductor device having the configuration illustrated in FIG. 16 is different from the semiconductor device having the configuration illustrated in FIG. 13A in including a data generation circuit 154.

The pixel 10 having the configuration illustrated in FIG. 15 can be used as the pixel 10 illustrated in FIG. 16. The wiring 155 electrically connected to the imaging circuit 100 is electrically connected to the data generation circuit 154. The data generation circuit 154 has a function of generating data that is to be supplied to the imaging circuit 100. Data generated by the data generation circuit 154 is supplied to the imaging circuit 100 through the wiring 155. Specifically, data generated by the data generation circuit 154 is supplied to the other electrode of the capacitor 105 included in the imaging circuit 100 through the wiring 155.

Figure 17:
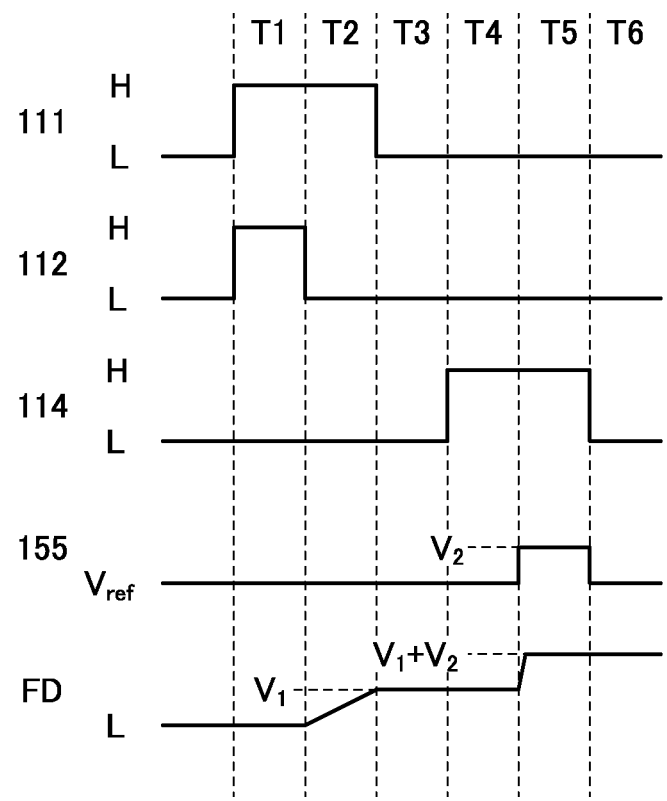
FIG. 17 is a diagram showing an example of an operation method of a semiconductor device.

FIG. 17 is a timing chart showing an example of an operation method of the imaging circuit 100 having the configuration illustrated in FIG. 15. Note that in the timing chart in this specification, "H" represents a high potential and "L" represents a low potential.

In a period T1, the potential of the wiring 111 and the potential of the wiring 112 are each set to a high potential and the potential of the wiring 114 is set to a low potential, whereby the transistor 101 and the transistor 102 are turned on and the transistor 104 is turned off. Accordingly, the potential of the node FD is reset to a low potential that is the potential of the wiring 122. The potential of the wiring 155 is a potential $V_{ref}$ that is a reference potential. The potential $V_{ref}$ can be a ground potential, for example. Hereinafter, the potential $V_{ref}$ is a ground potential.

In a period T2, the potential of the wiring 111 is set to a high potential, and the potential of the wiring 112 and the potential of the wiring 114 are each set to a low potential, whereby the transistor 101 is turned on and the transistor 102 and the transistor 104 are turned off. Accordingly, the potential of the node FD increases in accordance with the amount of light exposure to the photoelectric conversion element 12. Note that the potential of the wiring 155 is kept at the potential $V_{ref}$.

In a period T3, the potential of the wiring 111, the potential of the wiring 112, and the potential of the wiring 114 are each set to a low potential, whereby the transistor 101, the transistor 102, and the transistor 104 are turned off. Accordingly, the potential of the node FD is determined and retained. In the above manner, imaging data is obtained. Here, the determined potential of the node FD is referred to as a potential $V_1$. Note that the potential of the wiring 155 is kept at the potential $V_{ref}$.

Using OS transistors with a low off-state current as the transistor 101 and the transistor 102 that are electrically connected to the node FD can suppress charge leakage from the node FD, and thus enables a longer-term retention of the imaging data obtained by the imaging circuit 100.

In a period T4, the potential of the wiring 111 and the potential of the wiring 112 are each set to a low potential and the potential of the wiring 114 is set to a high potential, whereby the transistor 101 and the transistor 102 are turned off and the transistor 104 is turned on. Accordingly, a current $I_{ref}$ represented by Formula (1) below flows through the wiring 124. Here, k is a proportionality constant and $V_{th}$ is the threshold voltage of the transistor 103. Note that the potential of the wiring 155 is kept at the potential $V_{ref}$.

[Formula 1]

$$I_{ref} = k(V_1 - V_{th})^2 \tag{1}$$

Then, in a period T5, the potential of the wiring 155 is set to a potential corresponding to data generated by the data generation circuit 154 illustrated in FIG. 16. When the potential is a potential $V_2$ and the capacitive coupling coefficient of the node FD is 1, the potential of the node FD is a potential "$V_1+V_2$". Accordingly, a current I represented by Formula (2) below flows through the wiring 124.

[Formula 2]

$$I = k(V_1 + V_2 - V_{th})^2 \tag{2}$$

After the current flowing through the wiring 124 takes a value represented by Formula (2), "$I_{ref}-I$" is calculated. The arithmetic operation can be performed using an arithmetic circuit (not illustrated in FIG. 16 or the like), for example. Note that hereinafter "$I_{ref}-I$" is expressed as $\Delta I$.

[Formula 3]

$$\begin{aligned}\Delta I &= I_{ref} - I \\ &= k\{(V_1 - V_{th})^2 - (V_1 + V_2 - V_{th})^2\} \\ &= k(V_1 - V_{th} + V_1 + V_2 - V_{th}) \\ &\quad (V_1 - V_{th} - V_1 - V_2 + V_{th}) \\ &= -kV_2(2V_1 + V_2 - 2V_{th})\end{aligned} \tag{3}$$

Next, a value obtained by subtracting $\Delta I_0$, which is "$I_{ref}-I$" without light exposure, from $\Delta I$ shown in Formula (3) is calculated. That is, "$\Delta I-\Delta I_0$" is calculated. The arithmetic operation can be performed using the arithmetic circuit or the like. Here, $\Delta I_0$ can be represented by Formula (4) below. Note that the potential of the node FD when the current flowing through the wiring 124 is $\Delta I_0$ is the potential of the wiring 122, and the potential is a ground potential.

[Formula 4]

$$\begin{aligned}\Delta I_0 &= k\{(-V_{th})^2 - (V_2 - V_{th})^2\} \\ &= k(-V_{th} + V_2 - V_{th})(-V_{th} - V_2 + V_{th}) \\ &= -kV_2(V_2 - 2V_{th})\end{aligned} \tag{4}$$

Thus, the "$\Delta I-\Delta I_0$" can be represented by Formula (5) below.

[Formula 5]

$$\begin{aligned}\Delta I - \Delta I_0 &= k\{-V_2(2V_1 + V_2 - 2V_{th}) + V_2(V_2 - 2V_{th})\} \\ &= -2kV_1V_2\end{aligned} \tag{5}$$

As described above, the value of current flowing through the wiring 124 corresponds to the product of the potential $V_1$ corresponding to imaging data obtained by the imaging circuit 100 and the potential $V_2$ corresponding to data supplied from the data generation circuit 154 to the imaging circuit 100. Thus, the data supplied from the data generation circuit 154 to the imaging circuit 100 can be added to the imaging data obtained by the imaging circuit 100. The above is the operation in the period T5.

In a period T6, the potentials of the wiring 111, the wiring 112, and the wiring 114 are each set to a low potential. Accordingly, the transistor 101, the transistor 102, and the transistor 104 are turned off. The above is the example of the operation method of the imaging circuit 100 having the configuration illustrated in FIG. 15.

<Structure Example of Transistor>

Figure 18A:
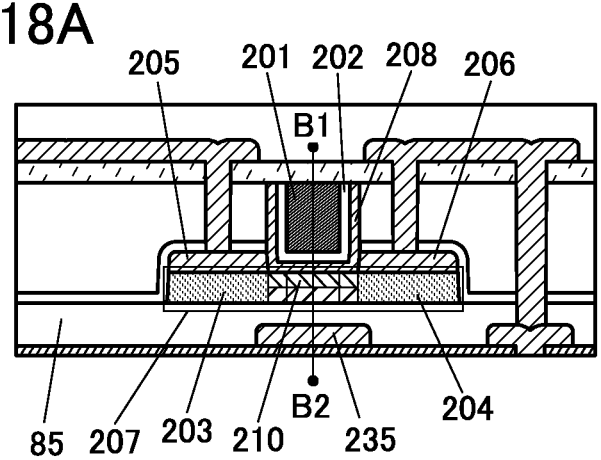
FIG. 18A to FIG. 18D are diagrams illustrating structure examples of a transistor.

FIG. 18A illustrates a detailed structure example of an OS transistor that can be used as the transistor 101 or the like. The OS transistor illustrated in FIG. 18A has a self-aligned structure in which an insulating layer is provided over a stack of a metal oxide layer and a conductive layer, and a groove reaching the metal oxide layer is provided in the insulating layer and the conductive layer to form a source electrode 205 and a drain electrode 206.

The OS transistor can have a structure including a gate electrode 201, a gate insulating layer 202, and a back gate electrode 235 in addition to a channel formation region 210, a source region 203, and a drain region 204 that are formed in a metal oxide layer 207. At least the gate insulating layer 202 and the gate electrode 201 are provided in the groove. A metal oxide layer 208 may be further provided in the groove. In addition, the insulating layer 85 has a function of a gate insulating layer of the back gate electrode 235.

Figure 18B:
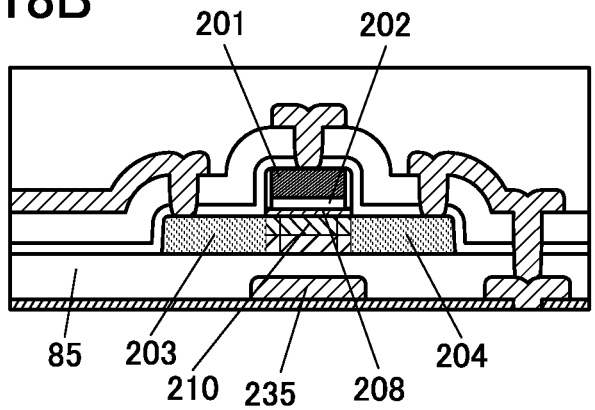

As illustrated in FIG. 18B, the OS transistor may have a self-aligned structure in which the source region 203 and the drain region 204 are formed in the metal oxide layer using the gate electrode 201 as a mask.

Figure 18C:
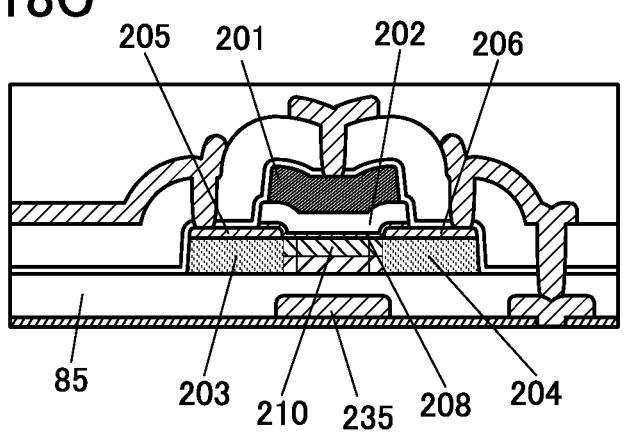

Alternatively, as illustrated in FIG. 18C, the OS transistor may be a non-self-aligned top-gate transistor including a region where the gate electrode 201 overlaps with the source electrode 205 or the drain electrode 206.

Figure 18D:
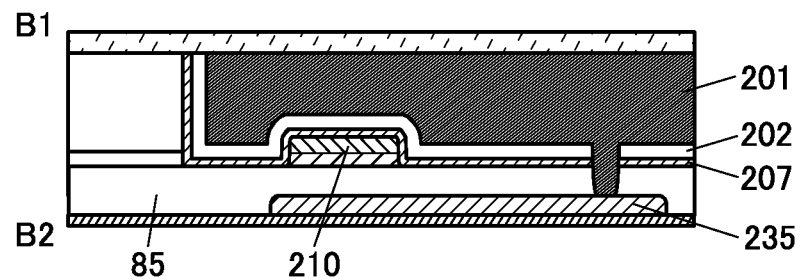

As illustrated in the cross-sectional view of the transistor in the channel width direction in FIG. 18D, the back gate electrode 235 may be electrically connected to the gate electrode 201 that is a front gate of the transistor, which is provided to face the back gate. Note that FIG. 18D illustrates the transistor in FIG. 18A as an example, but the same applies to transistors having other structures. The back gate electrode 235 may be supplied with a fixed potential that is different from that supplied to the front gate.

This embodiment can be combined with any of the other embodiments as appropriate.

Embodiment 3

In this embodiment, the composition of a CAC (Cloud-Aligned Composite)-OS that can be used for a transistor disclosed in one embodiment of the present invention will be described.

The CAC-OS is, for example, a composition of a material in which elements that constitute a metal oxide are unevenly distributed to have a size of greater than or equal to 0.5 nm and less than or equal to 10 nm, preferably greater than or equal to 1 nm and less than or equal to 2 nm, or a similar size. Note that in the following description, a state in which one or more metal elements are unevenly distributed and regions including the metal element(s) are mixed to have a size of greater than or equal to 0.5 nm and less than or equal to 10 nm, preferably greater than or equal to 1 nm and less than or equal to 2 nm, or a similar size in a metal oxide is referred to as a mosaic pattern or a patch-like pattern.

Note that the metal oxide preferably contains at least indium. In particular, indium and zinc are preferably contained. Moreover, in addition to these, one kind or a plurality of kinds selected from aluminum, gallium, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like may be contained.

For example, a CAC-OS in an In—Ga—Zn oxide (an In—Ga—Zn oxide in the CAC-OS may be particularly referred to as CAC-IGZO) has a composition in which materials are separated into indium oxide (hereinafter referred to as $InO_{X1}$ (X1 is a real number greater than 0)), indium zinc oxide (hereinafter referred to as $In_{X2}Zn_{Y2}O_{Z2}$ (each of X2, Y2, and Z2 is a real number greater than 0)), or the like and gallium oxide (hereinafter referred to as $GaO_{X3}$ (X3 is a real number greater than 0)), gallium zinc oxide (hereinafter referred to as $Ga_{X4}Zn_{Y4}O_{Z4}$ (each of X4, Y4, and Z4 is a real number greater than 0)), or the like so that a mosaic pattern is formed, and mosaic-like $InO_{X1}$ or $In_{X2}Zn_{Y2}O_{Z2}$ is evenly distributed in the film (this composition is hereinafter also referred to as a cloud-like composition).

That is, the CAC-OS is a composite metal oxide with a composition in which a region including $GaO_{X3}$ as a main component and a region including $In_{X2}Zn_{Y2}O_{Z2}$ or $InO_{X1}$ as a main component are mixed. Note that in this specification, when the atomic ratio of In to an element M in a first region is greater than the atomic ratio of In to an element M in a second region, for example, the first region is described as having higher In concentration than the second region.

Note that IGZO is a common name and sometimes refers to one compound formed of In, Ga, Zn, and O. A typical example is a crystalline compound represented by $InGaO_3(ZnO)_{m1}$ (m1 is a natural number) and a crystalline compound represented by $In_{(1+x0)}Ga_{(1-x0)}O_3(ZnO)_{m0}$ ($-1 \leq x0 \leq 1$; m0 is a given number).

The above crystalline compound has a single crystal structure, a polycrystalline structure, or a CAAC (C-Axis Aligned Crystalline) structure. Note that the CAAC structure is a crystal structure in which a plurality of IGZO nanocrystals have c-axis alignment and are connected in the a-b plane direction without alignment.

Meanwhile, the CAC-OS relates to the material composition of a metal oxide. In the material composition of a CAC-OS containing In, Ga, Zn, and O, some regions that contain Ga as a main component and are observed as nanoparticles and some regions that contain In as a main component and are observed as nanoparticles are each randomly dispersed in a mosaic pattern. Therefore, the crystal structure is a secondary element for the CAC-OS.

Note that in the CAC-OS, a stacked-layer structure including two or more kinds of films with different atomic ratios is not included. For example, a two-layer structure of a film containing In as a main component and a film containing Ga as a main component is not included.

A boundary between the region including $GaO_{X3}$ as a main component and the region including $In_{X2}Zn_{Y2}O_{Z2}$ or $InO_{X1}$ as a main component is not clearly observed in some cases.

Note that in the case where one kind or a plurality of kinds selected from aluminum, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like are contained instead of gallium, the CAC-OS refers to a composition in which some regions that contain the metal element(s) as a main component and are observed as nanoparticles and some regions that contain In as a main component and are observed as nanoparticles are each randomly dispersed in a mosaic pattern.

The CAC-OS can be formed by a sputtering method under a condition where a substrate is not heated intentionally, for example. In the case of forming the CAC-OS by a sputtering method, one or more selected from an inert gas (typically, argon), an oxygen gas, and a nitrogen gas may be used as a deposition gas. The ratio of the flow rate of the oxygen gas to the total flow rate of the deposition gas in deposition is preferably as low as possible; for example, the flow rate ratio of the oxygen gas is higher than or equal to 0% and lower than 30%, preferably higher than or equal to 0% and lower than or equal to 10%.

The CAC-OS is characterized in that a clear peak is not observed when measurement is conducted using a θ/2θ scan by an out-of-plane method, which is an X-ray diffraction (XRD) measurement method. That is, it is found from the X-ray diffraction measurement that no alignment in the a-b plane direction and the c-axis direction is observed in the measured region.

In an electron diffraction pattern of the CAC-OS which is obtained by irradiation with an electron beam with a probe diameter of 1 nm (also referred to as a nanobeam electron beam), a ring-like region with high luminance (a ring region) and a plurality of bright spots in the ring region are observed. Thus, the electron diffraction pattern indicates that the crystal structure of the CAC-OS includes a nanocrystal (nc) structure with no alignment in a plan-view direction and a cross-sectional direction.

Moreover, for example, it can be confirmed by EDX mapping obtained using energy dispersive X-ray spectroscopy (EDX) that the CAC-OS in the In—Ga—Zn oxide has a composition in which regions including $GaO_{X3}$ as a main component and regions including $In_{X2}Zn_{Y2}O_{Z2}$ or $InO_{X1}$ as a main component are unevenly distributed and mixed.

The CAC-OS has a structure different from that of an IGZO compound in which metal elements are evenly distributed, and has characteristics different from those of the IGZO compound. That is, the CAC-OS has a composition in which regions including $GaO_{X3}$ or the like as a main component and regions including $In_{X2}Zn_{Y2}O_{Z2}$ or $InO_{X1}$ as a main component are phase-separated from each other, and the regions including the respective elements as the main components form a mosaic pattern.

Here, a region including $In_{X2}Zn_{Y2}O_{Z2}$ or $InO_{X1}$ as a main component is a region with higher conductivity than a region including $GaO_{X3}$ or the like as a main component. In other words, when carriers flow through regions including $In_{X2}Zn_{Y2}O_{Z2}$ or $InO_{X1}$ as a main component, the conductivity of a metal oxide is exhibited. Accordingly, when regions including $In_{X2}Zn_{Y2}O_{Z2}$ or $InO_{X1}$ as a main component are distributed in a metal oxide like a cloud, high field-effect mobility (μ) can be achieved.

By contrast, a region including $GaO_{X3}$ or the like as a main component is a region with higher insulating property than a region including $In_{X2}Zn_{Y2}O_{Z2}$ or $InO_{X1}$ as a main component. In other words, when regions including $GaO_{X3}$ or the like as a main component are distributed in a metal oxide, leakage current can be suppressed and favorable switching operation can be achieved.

Accordingly, when the CAC-OS is used in a semiconductor element, the insulating property derived from $GaO_{X3}$ or the like and the conductivity derived from $In_{X2}Zn_{Y2}O_{Z2}$ or $InO_{X1}$ complement each other, whereby high on-state current ($I_{on}$) and high field-effect mobility (μ) can be achieved.

A semiconductor element using a CAC-OS has high reliability. Thus, the CAC-OS is suitably used in a variety of semiconductor devices typified by a display.

This embodiment can be combined with any of the other embodiments as appropriate.

Embodiment 4

In this embodiment, examples of an electronic device that can use a semiconductor device of one embodiment of the present invention will be described.

Figure 19A:
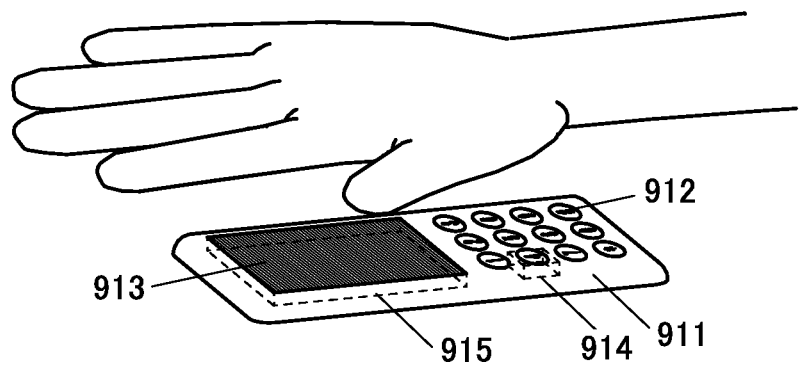
FIG. 19A to FIG. 19C are diagrams each illustrating an electronic device.

FIG. 19A illustrates a biometric authentication device including a housing 911, operation buttons 912, a sensor portion 913, and the like. When a hand or a finger is held over or put on the sensor portion 913, a form of vein can be recognized. The sensor portion 913 can also display an image. The obtained data can be transmitted to a server by a wireless communication unit 914 and compared with a database, so that an individual can be specified. Furthermore, a security code or the like can be input with the operation buttons.

The semiconductor device of one embodiment of the present invention is placed directly under the sensor portion 913. Thus, the detection sensitivity of the sensor portion 913 can be increased and a high-luminance image can be displayed on the sensor portion 913.

Figure 19B:
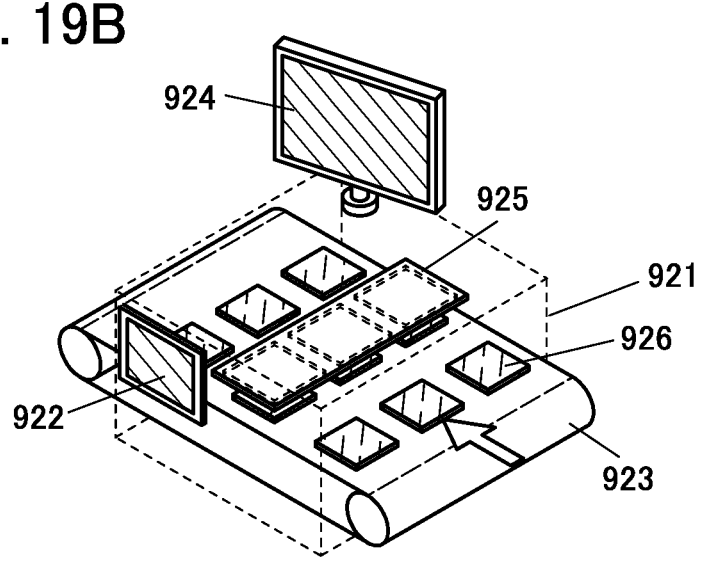

FIG. 19B illustrates a non-destructive inspection device including a housing 921, an operation panel 922, a transfer mechanism 923, a monitor 924, a sensor unit 925, and the like. Inspection members 926 are transported to the position directly under the sensor unit 925 by the transport mechanism 923. Images of the inspection members 926 are captured by the semiconductor device of one embodiment of the present invention provided in the sensor unit 925, and the captured images are displayed on the monitor 924. After that, the inspection members 926 are transported to an exit of the housing 921 and a defective member is separately collected.

The semiconductor device of one embodiment of the present invention is placed directly under the sensor unit 925. Accordingly, the detection sensitivity of the sensor unit 925 can be increased.

Figure 19C:
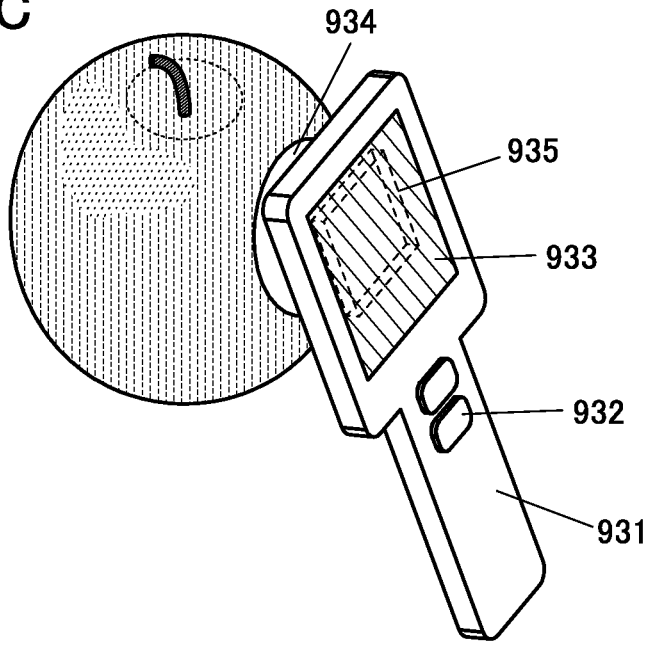

FIG. 19C illustrates a food-sorting device including a housing 931, operation buttons 932, a display portion 933, a light-blocking hood 934, and the like. Imaging is performed with the light-blocking hood 934, which is provided around a light-receiving portion, being in close contact with a target inspection food such as a fruit, whereby a foreign substance or an insect mixed in the food, a cavity or rot inside the food, and the like can be detected. In addition, sugar content, moisture content, and the like can also be detected from the intensity of the detected infrared light or the like. With the food-sorting device, defective products and grades can be sorted and the harvest time can be determined.

The semiconductor device of one embodiment of the present invention can be provided in the light-receiving portion. Accordingly, the light detection sensitivity of the light-receiving portion can be increased. Note that the structure illustrated in FIG. 19B may be used for the food-sorting device. Alternatively, the structure illustrated in FIG. 19C may be used for the non-destructive inspection device.

This embodiment can be combined with any of the other embodiments as appropriate.

Embodiment 5

In this embodiment, a market image where the semiconductor device of one embodiment of the present invention can be used will be described.

<Market Image>

Figure 20:
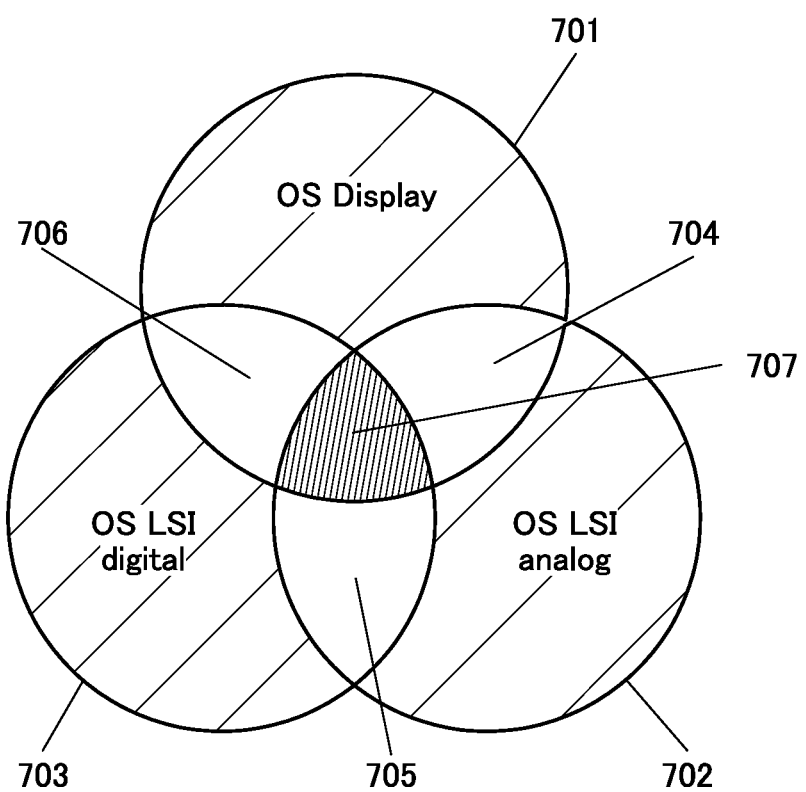
FIG. 20 is a diagram illustrating a market image.

FIG. 20 illustrates a market image where the semiconductor device of one embodiment of the present invention can be used. In FIG. 20, a region 701 represents a product field (OS Display) applicable to a display using a transistor including an oxide semiconductor in a channel formation region; a region 702 represents a product field (OS LSI analog) where an LSI (Large Scale Integration) using a transistor including an oxide semiconductor in a channel formation region can be applied to an analog one; and a region 703 represents a product field (OS LSI digital) where an LSI using a transistor including an oxide semiconductor in a channel formation region can be applied to a digital one. The semiconductor device of one embodiment of the present invention can be favorably used in the three regions: the region 701, the region 702, and the region 703 illustrated in FIG. 20, in other words, three big markets.

In FIG. 20, a region 704 represents a region where the region 701 and the region 702 overlap with each other; a region 705 represents a region where the region 702 and the region 703 overlap with each other; a region 706 represents a region where the region 701 and the region 703 overlap with each other; and a region 707 represents a region where the region 701, the region 702, and the region 703 overlap with one another.

In OS Display, an FET structure such as a bottom-gate OS FET (BG OSFET) or a top-gate OS FET (TG OS FET) can be favorably used. Note that the bottom-gate OS FET includes a channel-etched FET and a channel-protective FET. In addition, the top-gate OS FET includes a TGSA (Top Gate Self-Aligned) FET.

In OS LSI analog and OS LSI digital, a gate-last OS FET (GL OS FET) can be favorably used, for example.

Note that the above-described transistors each include a single-gate transistor with one gate electrode, a dual-gate transistor with two gate electrodes, or a transistor with three or more gate electrodes. Among dual-gate transistors, it is particularly preferable to use an S-channel (surrounded channel) transistor.

Note that in this specification and the like, an S-channel transistor refers to a transistor with a structure in which a channel formation region is electrically surrounded by the electric fields of one of a pair of gate electrodes and the other thereof.

As products included in OS display (the region 701), products in which an LCD (liquid crystal display), EL (Electro Luminescence), and an LED (Light Emitting Diode) are included as display elements can be given. Any of the above display elements is favorably combined with Q-Dot (Quantum Dot).

Note that in this embodiment, EL includes organic EL and inorganic EL. In addition, in this embodiment, LED includes a micro LED, a mini LED, and a macro LED. Note that in this specification and the like, a light-emitting diode with a chip size of 10000 μm$^2$ or less is referred to as a micro LED, a light-emitting diode with a chip size of greater than 10000 μm$^2$ and less than or equal to 1 mm$^2$ is referred to as a mini LED, and a light-emitting diode with a chip size of greater than 1 mm$^2$ is referred to as a macro LED, in some cases.

As products included in OS LSI analog (the region 702), a sound-source identification device that covers a wide frequency range (e.g., an audible sound with a frequency of 20 Hz to 20 kHz inclusive or ultrasonic wave of 20 kHz or greater), a battery control device (a battery control IC, a battery protection IC, or a battery management system), and the like can be given.

As products included in OS LSI digital (the region 703), a memory device, a CPU (Central Processing Unit) device, a GPU (Graphics Processing Unit) device, an FPGA (field-programmable gate array) device, a power device, a hybrid device in which an OS LSI and an Si LSI are stacked or mixed, a light-emitting element, and the like can be given.

As products included in the region 704, a display element including an infrared ray sensor or a near-infrared ray sensor in a display region, a sensor-equipped signal processing device including an OS FET, an implantable biosensor device, and the like can be given. As products included in the region 705, a processing circuit including an A/D (Analog to Digital) conversion circuit or the like, an AI (Artificial Intelligence) device including the processing circuit, and the like can be given. As products included in the region 706, a display device using a Pixel AI technology can be given, for example. Note that in this specification and the like, the Pixel AI technology refers to a technology utilizing a memory composed of an OS FET or the like included in a pixel circuit of a display.

As a product included in the region 707, a composite that combines a variety of products included in the region 701 to the region 706 can be given.

As described above, the semiconductor device of one embodiment of the present invention can be applied to a variety of product fields, as illustrated in FIG. 20. That is, the semiconductor device of one embodiment of the present invention can be applied to a lot of markets.

Note that the structures described in this embodiment can be implemented in combination with any of the other embodiments described in this specification and the like as appropriate.

This embodiment can be combined with any of the other embodiments as appropriate.

REFERENCE NUMERALS

10: pixel, 10B: pixel, 10G: pixel, 10IR: pixel, 10R: pixel, 11: substrate, 12: photoelectric conversion element, 13: low-resistance region, 14: conductive layer, 21: conductive layer, 22: conductive layer, 23: conductive layer, 24: conductive layer, 30: substrate, 31: conductive layer, 32: insulating layer, 33: insulating layer, 34: low-resistance region, 40: light-emitting element, 41: conductive layer, 42: EL layer, 42a: EL layer, 42b: EL layer, 42c: EL layer, 43: conductive layer, 44: charge generation layer, 44a: charge generation layer, 44b: charge generation layer, 45: conductive layer, 46: active layer, 50: substrate, 51: filter, 51B: filter, 51G: filter, 51IR: filter, 51R: filter, 52: sealing layer, 53: filter, 54: microlens, 55: microlens, 56: light control layer, 60: substrate, 61: layer, 62: layer, 63: layer, 64: layer, 71: hole-injection layer, 72: hole-transport layer, 73: light-emitting layer, 74: electron-transport layer, 75: electron-injection layer, 80: insulating layer, 81: insulating layer, 82: insulating layer, 83: insulating layer, 84: insulating layer, 85: insulating layer, 86: insulating layer, 87: insulating layer, 100: imaging circuit, 101: transistor, 102: transistor, 103: transistor, 104: transistor, 105: capacitor, 111: wiring, 112: wiring, 114: wiring, 121: wiring, 122: wiring, 124: wiring, 125: wiring, 130: display circuit, 131: transistor, 132: transistor, 133: transistor, 134: capacitor, 141: wiring, 142: wiring, 143: wiring, 144: wiring, 145: wiring, 151: pixel array, 152: gate driver circuit, 153: source driver circuit, 154: data generation circuit, 155: wiring, 201: gate electrode, 202: gate insulating layer, 203: source region, 204: drain region, 205: source electrode, 206: drain electrode, 207: metal oxide layer, 208: metal oxide layer, 210: channel formation region, 235: back gate electrode, 610: arithmetic device, 611: arithmetic portion, 612: memory portion, 620: input/output device, 660: reading portion, 670: electric lock, 701: region, 702: region, 703: region, 704: region, 705: region, 706: region, 707: region, 911: housing, 912: operation button, 913: sensor portion, 914: wireless communication unit, 921: housing, 922: operation panel, 923: transfer mechanism, 924: monitor, 925: sensor unit, 926: inspection member, 931: housing, 932: operation button, 933: display portion, 934: light-blocking hood

The invention claimed is:

1. An authentication system comprising:
an arithmetic device; and
an input/output device,
wherein the arithmetic device supplies first control data and second control data,
wherein the arithmetic device is supplied with a sensor signal,
wherein the input/output device comprises an electric lock and a reading portion,
wherein the electric lock is unlocked on the basis of the second control data,
wherein the reading portion is supplied with the first control data and supplies the sensor signal,
wherein the reading portion comprises a light-emitting element and a pixel array,
wherein the light-emitting element emits light comprising infrared rays,
wherein the pixel array comprises pixels,
wherein the pixels each comprise an imaging circuit and a photoelectric conversion element,
wherein the pixel comprises a first layer and a second layer,
wherein the first layer comprises a first transistor and a second transistor,
wherein the second layer comprises a light-emitting element and a photoelectric conversion element,
wherein one of a source and a drain of the first transistor is electrically connected to one electrode of the light-emitting element, and one of a source and a drain of the second transistor is electrically connected to one electrode of the photoelectric conversion element,
wherein the imaging circuit is electrically connected to the photoelectric conversion element,
wherein the imaging circuit comprises a third transistor, and
wherein the third transistor comprises an oxide semiconductor film.

2. The authentication system according to claim 1,
wherein the arithmetic device comprises an arithmetic portion and a memory portion,
wherein the memory portion stores a program and a first database,
wherein the arithmetic portion extracts a feature value from the sensor signal on the basis of the program,
wherein the arithmetic portion examines the feature value using the first database, and
wherein the arithmetic portion supplies the second control data on the basis of an examination result.

3. The authentication system according to claim 2,
wherein the memory portion stores a second database, and
wherein the arithmetic portion records an unlocking history in the second database on the basis of the examination result.

4. The authentication system according to claim 1,
wherein the oxide semiconductor film comprises In, Zn, and M(M is Al, Ti, Ga, Sn, Y, Zr, La, Ce, Nd, or Hf).

5. A method for recording an unlocking history of an authentication system comprising:
an input device/output device,
wherein the input/output device comprises a reading portion,
wherein the reading portion comprises a light-emitting element and a pixel array,
wherein the pixel comprises a first layer and a second layer,
wherein the first layer comprises a first transistor and a second transistor,
wherein the second layer comprises a light-emitting element and a photoelectric conversion element,
wherein the method for recording the unlocking history comprises a first step to a seventh step,
wherein imaging is performed by the reading portion,
wherein in the first step, imaging is performed to obtain a sensor signal,
wherein in the second step, a program proceeds to the third step in the case where a change exceeding a predetermine level is observed in the sensor signal and the program proceeds to the first step in the case where only a change less than or equal to the predetermined level is observed,
wherein in the third step, imaging is performed to obtain a sensor signal,
wherein in the fourth step, a feature value is extracted from the sensor signal which was obtained in the third step,
wherein in the fifth step, the feature value is examined using a first database, and the program proceeds to the sixth step in the case where the first database comprises data matching the feature value and the program proceeds to the first step in the case where the first database comprises no data matching the feature value,
wherein in the sixth step, second control data is supplied to unlock an electric lock,
wherein in the seventh step, the unlocking history is recorded in a second database,
wherein the reading portion comprises a light-emitting element and a pixel array,
wherein the pixel array comprises pixels, and
wherein the pixels each comprise an imaging circuit and a photoelectric conversion element.

6. The authentication system according to claim 2,
wherein the pixel comprises a first layer and a second layer,
wherein the first layer comprises a first transistor and a second transistor,
wherein the second layer comprises a light-emitting element and a photoelectric conversion element, and
wherein one of a source and a drain of the first transistor is electrically connected to one electrode of the light-emitting element, and one of a source and a drain of the second transistor is electrically connected to one electrode of the photoelectric conversion element.

7. The authentication system according to claim 2,
wherein the oxide semiconductor film comprises In, Zn, and M(M is Al, Ti, Ga, Sn, Y, Zr, La, Ce, Nd, or Hf).

* * * * *